(12) United States Patent
Madhani et al.

(10) Patent No.: US 11,045,597 B2
(45) Date of Patent: Jun. 29, 2021

(54) EXTRACORPOREAL AMBULATORY ASSIST LUNG

(71) Applicants: University of Pittsburgh—Of the Commonwealth System of Higher Education, Pittsburgh, PA (US); Carnegie Mellon University, Pittsburgh, PA (US); Mississippi State University, Starkville, MS (US)

(72) Inventors: Shalv Madhani, Pittsburgh, PA (US); Brian Joseph Frankowski, Imperial, PA (US); William J. Federspiel, Pittsburgh, PA (US); Gregory Burgreen, Starkville, MS (US); James F. Antaki, Allison Park, PA (US)

(73) Assignees: University of Pittsburgh—Of the Commonwealth System of Higher Education, Pittsburgh, PA (US); Carnegie Mellon University, Pittsburgh, PA (US); Mississippi State University, Starkville, MS (US)

( * ) Notice: Subject to any disclaimer, the term of this patent is extended or adjusted under 35 U.S.C. 154(b) by 448 days.

(21) Appl. No.: 15/738,406

(22) PCT Filed: Jun. 23, 2016

(86) PCT No.: PCT/US2016/038957
§ 371 (c)(1),
(2) Date: Dec. 20, 2017

(87) PCT Pub. No.: WO2016/210089
PCT Pub. Date: Dec. 29, 2016

(65) Prior Publication Data
US 2018/0185567 A1   Jul. 5, 2018
US 2018/0353673 A9   Dec. 13, 2018

Related U.S. Application Data

(60) Provisional application No. 62/183,730, filed on Jun. 23, 2015.

(51) Int. Cl.
*A61M 1/36* (2006.01)
*A61M 1/16* (2006.01)
(Continued)

(52) U.S. Cl.
CPC ........ *A61M 1/3667* (2014.02); *A61M 1/1625* (2014.02); *A61M 1/1698* (2013.01);
(Continued)

(58) Field of Classification Search
CPC .............. A61M 1/3667; A61M 1/3666; A61M 1/1013; A61M 1/1625; A61M 1/1036;
(Continued)

(56) References Cited

U.S. PATENT DOCUMENTS 5,360,317 A * 11/1994 Clausen .............. F04D 29/0413
415/206
6,117,390 A * 9/2000 Corey, Jr. ........... A61M 1/1698
422/44
(Continued)

FOREIGN PATENT DOCUMENTS

WO  WO2006031858 A1   3/2006
WO  WO2006118817 A1   11/2006
(Continued)

OTHER PUBLICATIONS

Wu, Z. J., et al., Progress toward an ambulatory pump-lung. The Journal of thoracic and cardiovascular surgery, 2005, 130(4), 973-978.
(Continued)

*Primary Examiner* — Nicholas J Weiss
*Assistant Examiner* — Alessandro R Del Priore
(74) *Attorney, Agent, or Firm* — Bartony & Associates, LLC

(57) ABSTRACT

An extracorporeal system for lung assist includes a housing which includes a blood flow inlet in fluid connection with a pressurizing stator compartment, a fiber bundle compartment in fluid connection with the pressurizing stator compartment via a flow channel within the housing, and a blood flow outlet in fluid connection with the fiber bundle compartment. An impeller is rotatably positioned within the pressurizing compartment. The system further includes a fiber bundle within the fiber bundle compartment. A plurality of hollow gas permeable fibers of the fiber bundle extend generally perpendicular to the direction of bulk flow of blood through the fiber bundle compartment from the flow channel to the blood flow outlet.

22 Claims, 29 Drawing Sheets

(51) Int. Cl.
| | |
|---|---|
| *A61M 60/113* | (2021.01) |
| *A61M 60/205* | (2021.01) |
| *A61M 60/82* | (2021.01) |
| *A61M 60/419* | (2021.01) |
| *A61M 60/818* | (2021.01) |
| *A61M 60/824* | (2021.01) |

(52) U.S. Cl.
CPC ........ *A61M 1/3666* (2013.01); *A61M 60/113* (2021.01); *A61M 60/419* (2021.01); *A61M 60/818* (2021.01); *A61M 60/82* (2021.01); *A61M 60/824* (2021.01); *A61M 60/205* (2021.01); *A61M 2205/7536* (2013.01)

(58) Field of Classification Search
CPC .............. A61M 1/1017; A61M 1/1015; A61M 1/1006; A61M 1/1698; A61M 1/101; A61M 2205/7536; A61M 1/14; A61M 1/25; A61M 1/28

See application file for complete search history.

(56) References Cited

U.S. PATENT DOCUMENTS

| | | | |
|---|---|---|---|
| 6,428,747 | B1 | 8/2002 | Dueri |
| 7,022,284 | B2 | 4/2006 | Brian |
| 7,871,566 | B2 | 1/2011 | Strauss |
| 8,187,216 | B2 | 5/2012 | Niitsuma |
| 2004/0219060 | A1* | 11/2004 | Maianti ............... A61M 1/3666 422/46 |
| 2004/0223872 | A1* | 11/2004 | Brian .................... A61M 1/262 422/45 |
| 2006/0155237 | A1* | 7/2006 | Vijay .................. A61M 1/3666 604/6.11 |
| 2008/0199357 | A1 | 8/2008 | Gellman |
| 2013/0343954 | A1 | 12/2013 | Gartner |
| 2014/0065016 | A1 | 3/2014 | Federspiel |
| 2014/0288354 | A1 | 9/2014 | Timms |
| 2016/0281743 | A1* | 9/2016 | Itamochi ............... F04D 29/426 |

FOREIGN PATENT DOCUMENTS

| | | | | |
|---|---|---|---|---|
| WO | WO-2014085620 | A1 * | 6/2014 | ............ A61M 1/101 |
| WO | WO2014085620 | A1 | 6/2014 | |
| WO | WO2016210089 | A1 | 12/2016 | |

OTHER PUBLICATIONS

Zhang, T. et al., A novel wearable pump-lung device: In vitro and acute in vivo study. The Journal of Heart and Lung Transplantation, (2012), 31(1), 101-105.

Wu, Z. J. et al.,Thirty-day in-vivo performance of a wearable artificial pump-lung for ambulatory respiratory support. The Annals of thoracic surgery, (2012), 93(1), 274-281.

Schewe, R. E. et al., In-parallel attachment of a low-resistance compliant thoracic artificial lung under rest and simulated exercise. The Annals of thoracic surgery, (2012), 94(5), 1688-1694.

ASAIO 2015 Oral presentation in Chicago (Jun. 25, 2015).

* cited by examiner

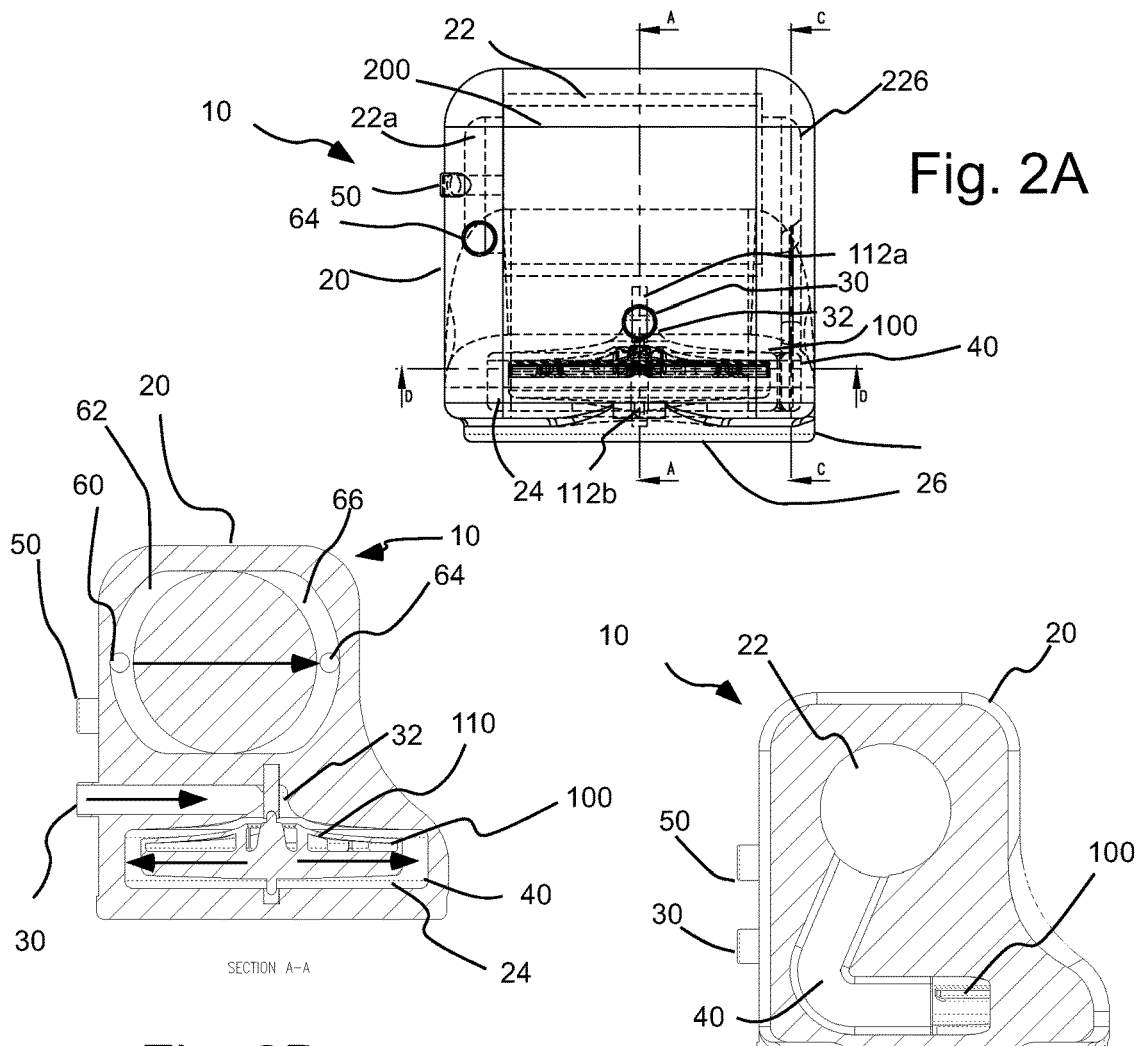
Fig. 2A
Fig. 2B
Fig. 2C
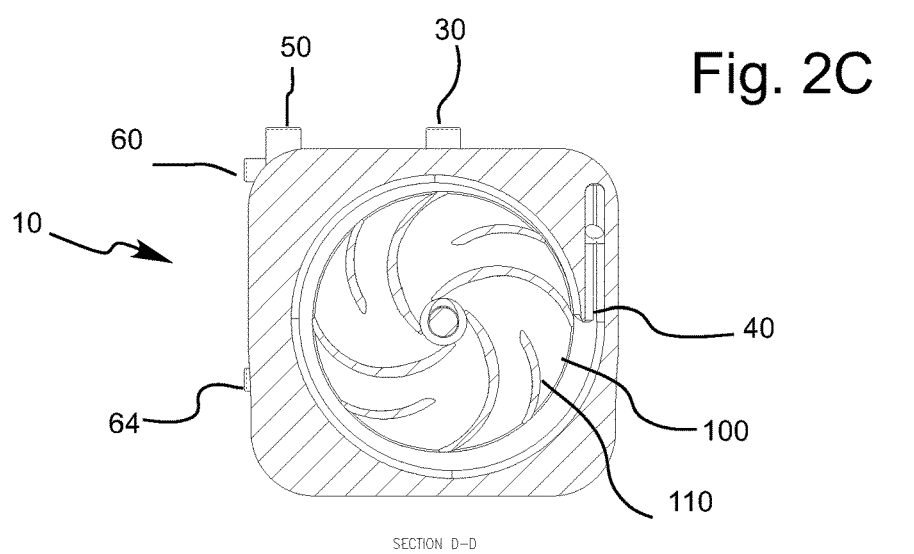
Fig. 2D

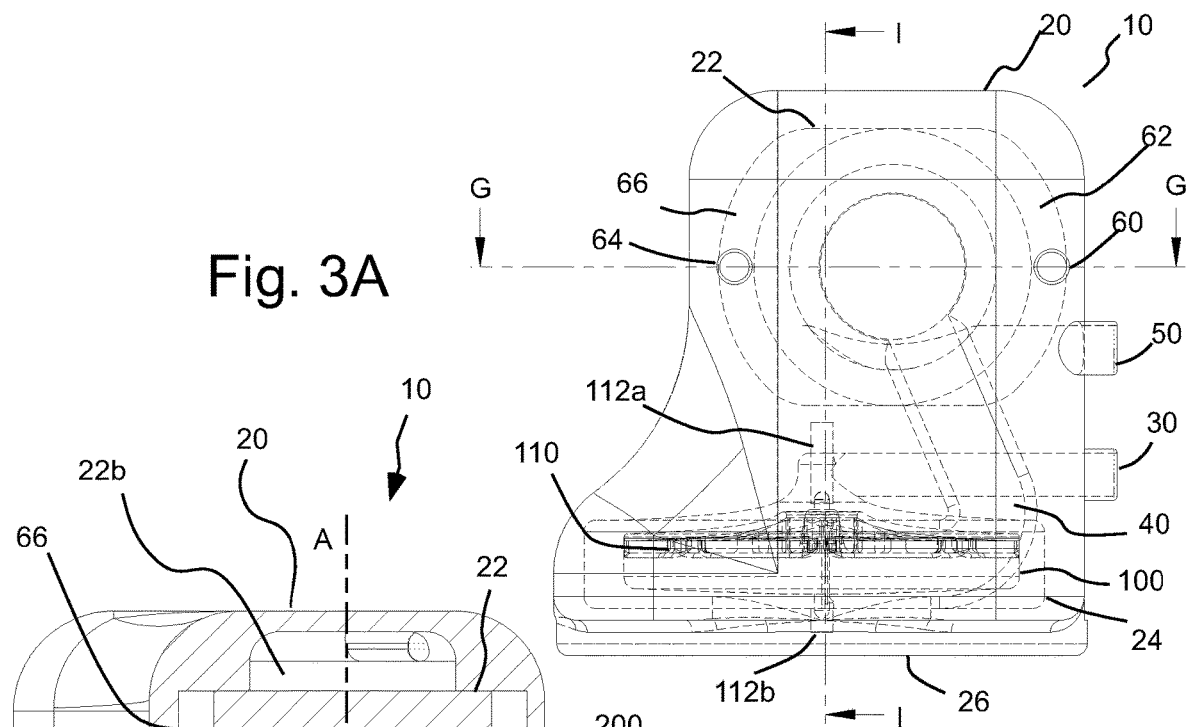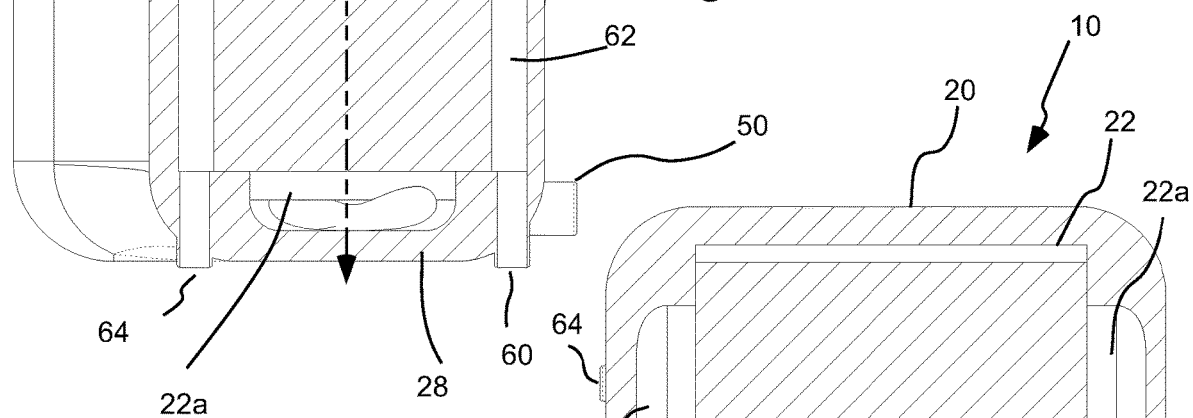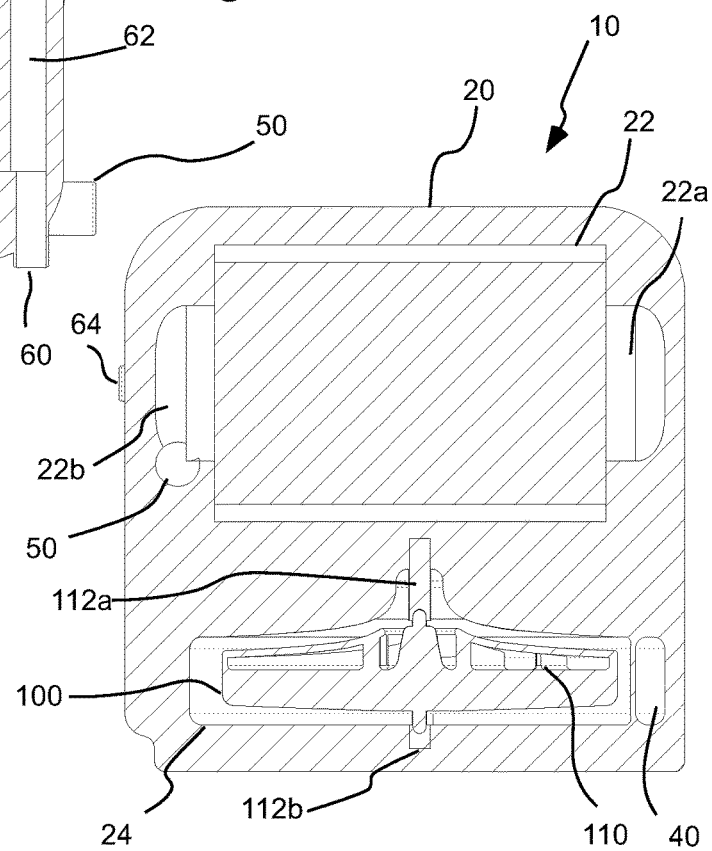

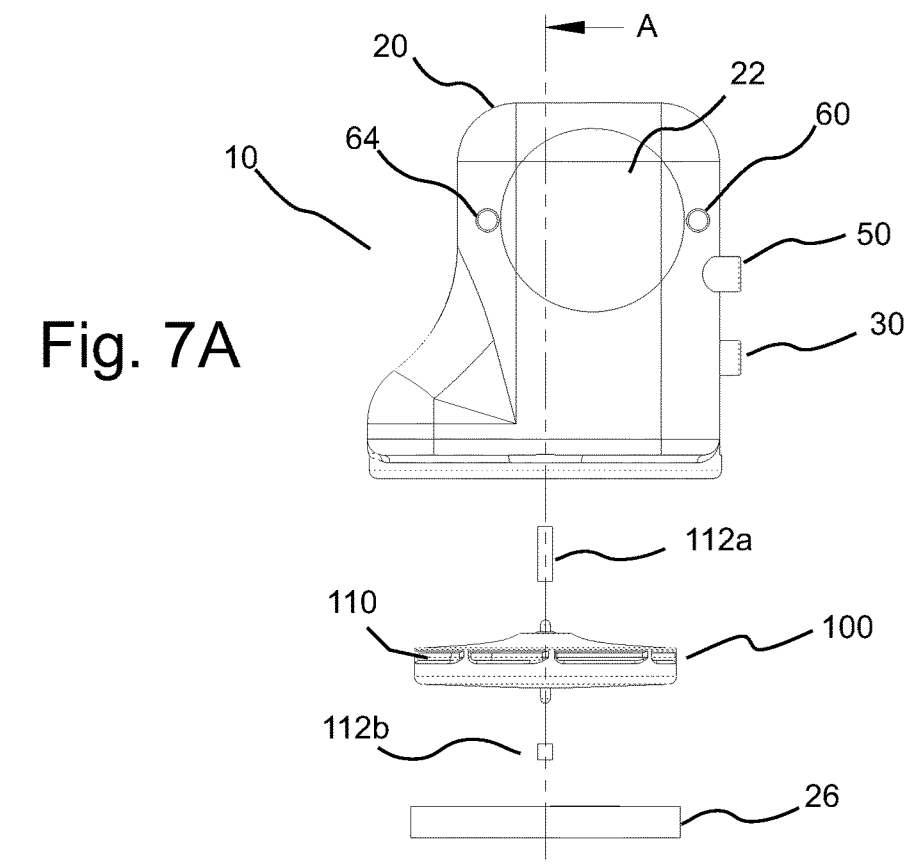
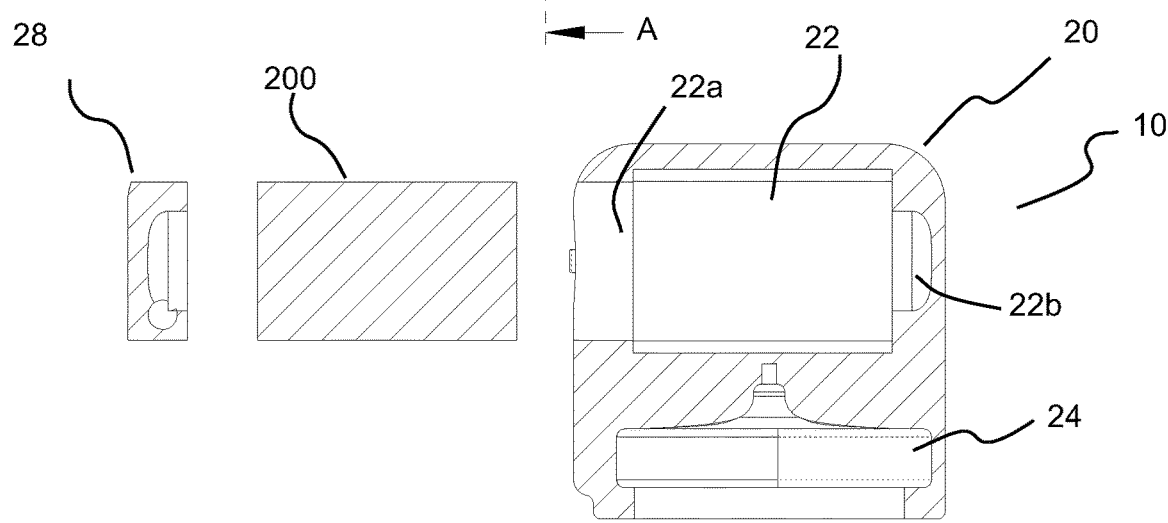
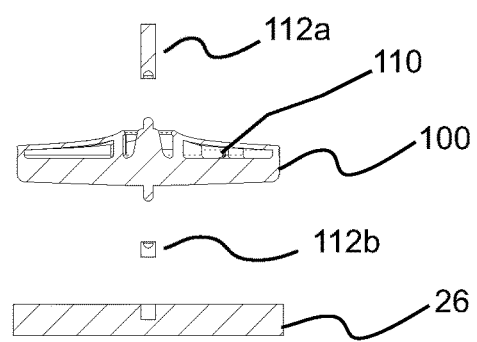

Fig. 7C
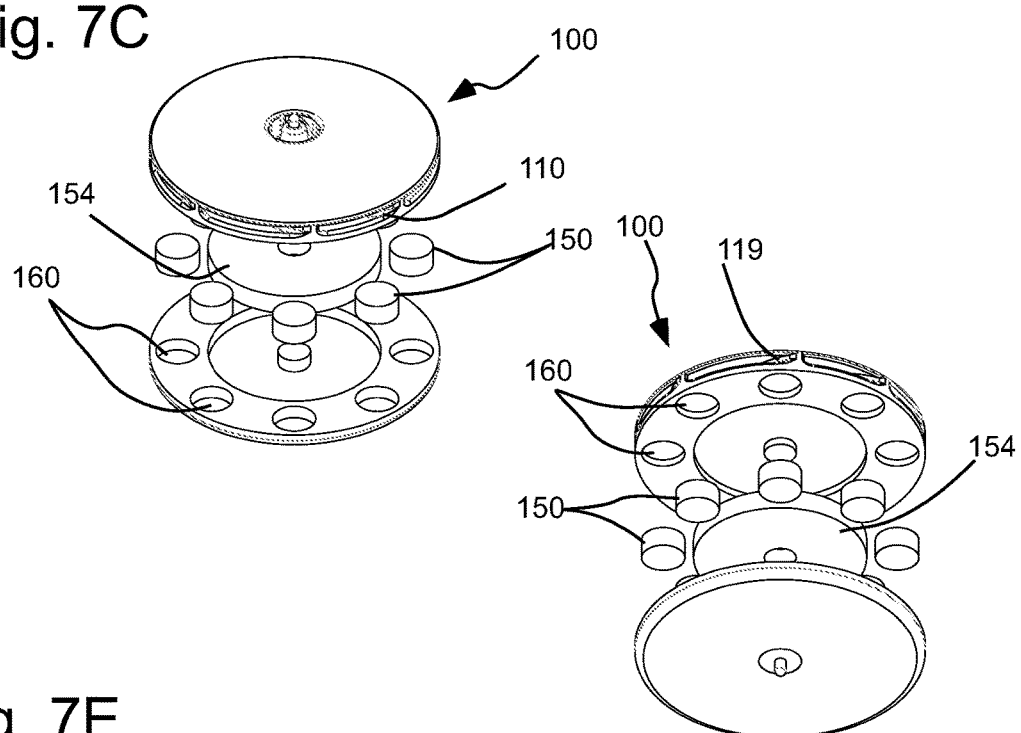
Fig. 7D
Fig. 7E
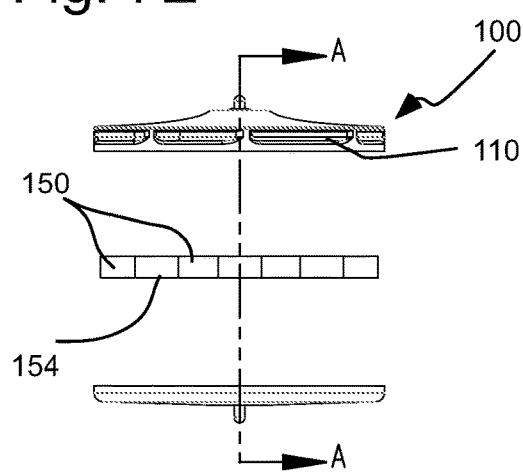
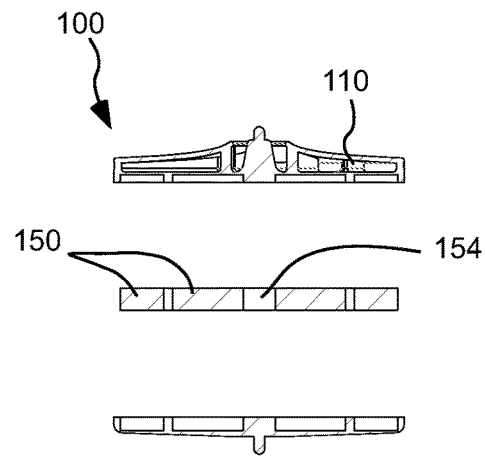
Fig. 7F

EXTRACORPOREAL AMBULATORY ASSIST LUNG

CROSS-REFERENCE TO RELATED APPLICATION

This application is a national phase filing of PCT International Patent Application No. PCT/US2016/038957, filed Jun. 23, 2016, which claims benefit of U.S. Provisional Patent Application Ser. No. 62/183,730, filed Jun. 23, 2015, the disclosures of which are incorporated herein by reference.

GOVERNMENTAL INTEREST

This invention was made with government support under grant nos. HL117637; DK045482; DK054936; DK078775; and HD056004 awarded by the National Institute of Health. The government has certain rights in this invention.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Acute and chronic diseases of the lung remain major healthcare problems. The American Lung Association reports that nearly 350,000 Americans die each year of some form of lung disease. Lung disease is the number three killer of Americans and is responsible for one in seven deaths. Acute lung failure and adult respiratory distress syndrome (ARDS) are prevalent forms of lung disease. ARDS afflicts about 150,000 Americans each year. The associated mortality of ARDS remains between 40 and 60% despite improvements in critical care medicine. Most lung disease, however, is chronic. Emphysema and chronic bronchitis, two forms of chronic obstructive pulmonary disease (COPD), afflict over 14 million Americans annually. Chronic lung disease is now the 3rd leading cause of death in America, claiming the lives of over 400,000 annually and carrying a cost of $154 billion. As chronic lung disease reaches end stage, lung transplantation becomes the only choice for effective treatment. Lung transplantation has had a steady rise over the last 10 years and ~3300 lung transplants are performed annually worldwide. The average time on the waiting list varies from 6 to 12 months depending on the patient's condition and institutional expertise, and 10-15% of patients die while on the waiting list in the US. A narrow window of opportunity exists for lung transplant in any patient who is sick enough to benefit from the operation, but healthy enough to survive months of waiting for a donor lung and then the subsequent surgery.

Once they reach a critical condition, mechanical ventilation and extracorporeal membrane oxygenation (ECMO) are the only alternatives for respiratory support available to bridge acute and chronic respiratory patients to lung recovery or lung transplantation. Mechanical ventilation (MV) may maintain adequate gas exchange for short term support, but in longer term support can lead to ventilator induced lung injury from barotrauma (high pressure), volutrauma (over-distension), and biotrauma (molecular and cell mediated inflammation), which can further worsen the respiratory status of the patient. ECMO is expensive and complicated, requiring the use of an external pump and blood circuit that have to be supervised continuously by highly trained technicians. The confinement of the patient in MV and especially ECMO leads to a progressive deconditioning that is reflected in higher postoperative complications and earlier mortality after transplant. Nevertheless, ECMO has been increasingly considered as the only alternative to bridge patients to lung transplant or lung recovery after an acute decompensation from their disease. More recently, with increasing experience at active transplant centers and improvement in ECMO technology, the concept of "ambulatory ECMO" has gained popularity and facilitates and expedites patient recovery after transplantation. Success in ambulatory ECMO underscores the importance of maintaining patient mobility. Currently available ambulatory ECMO systems combine existing blood pumps and bypass oxygenators into an integrated system, but remain bulky and cumbersome and require frequent exchange of the oxygenators for longer term support.

Recent success with paracorporeal left ventricular assist devices (VADs) for heart failure patients has stimulated envisioning an ambulatory pump-lung device that can be a bridge to lung transplant or recovery. No fully integrated ambulatory pump-lungs are being used clinically, however. Portable or ambulatory systems under development integrate a separate blood pump and oxygenator under a single controller unit, but remain cumbersome. In such devices, a blood pump is typically connected by one or more conduits (for example, lengths of tubing) to an oxygenator. While a number of systems have integrated blood pumps, the blood leaving the impeller unit of these devices typically travels through channels before being distributed by manifolds into the hollow fiber bundle compartment.

SUMMARY

In one aspect, an extracorporeal system for lung assist includes a housing which includes a blood flow inlet in fluid connection with a pressurizing stator compartment, a fiber bundle compartment in fluid connection with the pressurizing stator compartment via a flow channel, and a blood flow outlet in fluid connection with the fiber bundle compartment. In a number of embodiment, the flow channel is formed within the housing. An impeller is rotatably positioned within the pressurizing stator compartment for pressurizing blood entering the pressurizing stator compartment from the blood flow inlet. The system further includes a fiber bundle positioned within the fiber bundle compartment. The fiber bundle includes a plurality of hollow gas permeable fibers. The plurality of hollow gas permeable fibers is adapted to permit diffusion of gas between blood and an interior of the hollow gas permeable fibers. The plurality of hollow gas permeable fibers is positioned such that blood flows around the plurality of hollow gas permeable fibers when flowing through the fiber bundle compartment. The plurality of hollow gas permeable fibers extend generally perpendicular to the direction of bulk flow of blood through the fiber bundle compartment from the flow channel to the blood flow outlet. The system further includes a gas inlet in fluid connection with the housing and in fluid connection with inlets of the plurality of hollow gas permeable fibers and a gas outlet in fluid connection with the housing and in fluid connection with outlets of the plurality of hollow gas permeable fibers. The system may, for example, be a paracorporeal system. Blood may be blocked from flowing to the gas inlet and the gas outlet.

The plurality of hollow gas permeable fibers may, for example, include a plurality of layers of fiber fabric, wherein each of the plurality of layers of fiber fabric includes hollow gas permeable fibers. In a number of embodiments, adjacent layers of fiber fabric are rotated relative to each other such that the orientation of the plurality of hollow gas permeable fibers in adjacent layers of fiber fabric are of a different orientation.

In a number of embodiments, the plurality of hollow gas permeable fibers is formed in at least one generally cylindrical bundle. The generally cylindrical bundle may, for example, be formed from a plurality of layers of fiber fabric, wherein each of the plurality of layers of fiber fabric includes hollow gas permeable fibers. Adjacent layers of fiber fabric may, for example, rotate relative to each other as described above such that the orientation of the plurality of hollow gas permeable fibers in adjacent layers of fiber fabric are of a different orientation.

In a number of embodiments, the mean velocity through the fiber bundle is at least 2 cm/sec, at least 2.5 cm/sec, at least 3 cm/sec or at least 3.5 cm/sec. In a number of embodiments, the mean velocity of blood through the fiber bundle is in the range of approximately 2 to 5 cm/sec. A cross-sectional area of the fiber bundle may, for example, be no more than 7.07 $in^2$, no more than 4.9 $in^2$, no more than 3.14 $in^2$, or no more than 2.4 $in^2$. The length or height of the fiber bundle may, for example, be at least 1.8 inches.

In a number of embodiments, the system includes a system to offset hydrodynamic force on the impeller. The system to offset hydrodynamic force may, for example, include a first magnet in operative connection with the impeller which cooperates with a second magnet to create a repellant force therebetween.

The system may, for example, be adapted to deliver flows in the range of approximately 2 to 4 liters per minute. The flow rate may, for example, be adjustable.

The housing, the fiber bundle compartment, the blood flow inlet, the blood flow outlet, the gas inlet, the gas outlet, the pressurizing stator compartment, and the flow channel between the pressurizing stator compartment and the fiber bundle compartment may, for example, be formed integrally.

In a number of embodiments, the blood flow inlet is in connection with the pressurizing stator compartment via a plenum. The flow channel may, for example, extend generally tangentially from the pressurizing stator compartment in a number of embodiments. In a number of embodiments, the flow channel extends generally tangentially (that is, tangentially or within 5 degrees of tangentially) from the pressurizing stator compartment.

The flow channel may, for example, be in fluid connection with a manifold in fluid connection with the fiber bundle compartment. In a number of embodiments, the flow channel extends in a curved path from the pressurizing stator compartment to the manifold.

In a number of embodiments, bulk flow of blood through the fiber bundle is in a generally axial direction (that is, axially or within 5 degrees of axially). The fiber bundle may, for example, be oriented in a manner to minimize the size or form factor of the system. In a number of embodiments, the axis of the fiber bundle is oriented generally parallel (that is, parallel or within 5 degrees of parallel) to a plane of rotation of the impeller.

In a number of embodiments, the system is no more than 12.7 cm (5 inches) in height, no more than 12.7 cm (5 inches) in width, and no more than 12.7 cm (5 inches) in length (exclusive of an externally coupled motor drive).

A method of extracorporeal lung assist to a patient includes providing a system as described above and elsewhere herein, connecting the blood flow inlet to the patient's vasculature, connecting the blood flow outlet to the patient's vasculature; and passing a sweep gas within lumens of the plurality of hollow gas permeable fibers via the gas inlet and the gas outlet. The system may, for example, be operated as a paracorporeal system.

The present devices, systems and methods, along with the attributes and attendant advantages thereof, will best be appreciated and understood in view of the following detailed description taken in conjunction with the accompanying drawings.

BRIEF DESCRIPTION OF THE DRAWINGS

FIG. 2A illustrates a front, hidden line view of the system of FIG. 1A.

FIG. 2B illustrates a section A-A (with reference to FIG. 2A) cross-sectional view of the system of FIG. 1A.

FIG. 2C illustrates a section C-C (with reference to FIG. 2A) cross-sectional view of the system of FIG. 1A.

FIG. 2D illustrates a section D-D (with reference to FIG. 2A) cross-sectional view of the system of FIG. 1A.

FIG. 3A illustrates a side, hidden line view of the system of FIG. 1A.

FIG. 3B illustrates a section G-G (with reference to FIG. 3A) cross-sectional view of the system of FIG. 1A.

FIG. 3C illustrates a section I-I (with reference to FIG. 3A) cross-sectional view of the system of FIG. 1A.

FIG. 7A illustrates a side, disassembled or exploded view of the system of FIG. 1A.

FIG. 7B illustrates a front, section A-A cross-sectional view (with reference to FIG. 7A) view of the system of FIG. 1A.

FIG. 7C illustrates a prospective, disassembled or exploded view of an embodiment of an impeller hereof, FIG. 7D illustrates another prospective, disassembled or exploded view of the impeller of FIG. 7C.

FIG. 7E illustrates a side, disassembled or exploded view of the impeller of FIG. 7C.

FIG. 7F illustrates a section A-A (see FIG. 7E) cross-sectional, disassembled or exploded view of the impeller of FIG. 7C.

DETAILED DESCRIPTION

Figure 1A:
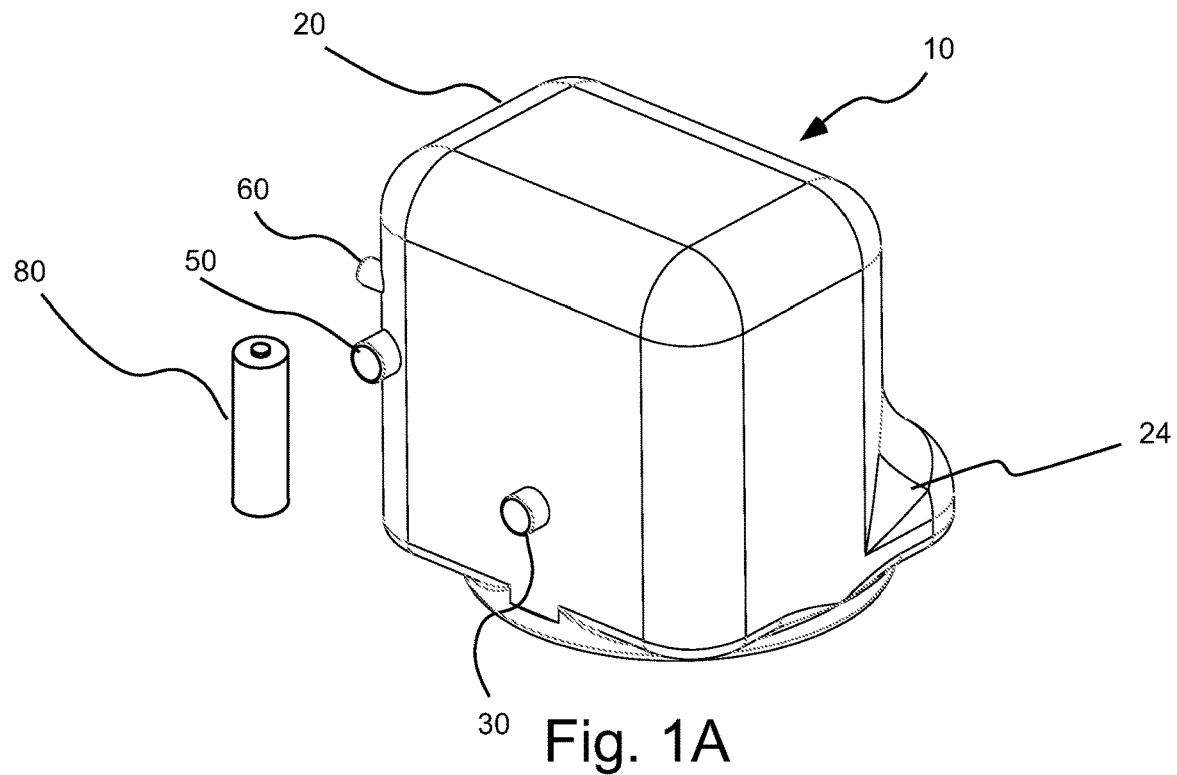
FIG. 1A illustrates a perspective view of an embodiment of a paracorporeal ambulatory assist lung apparatus, device or system hereof.
Figure 1B:
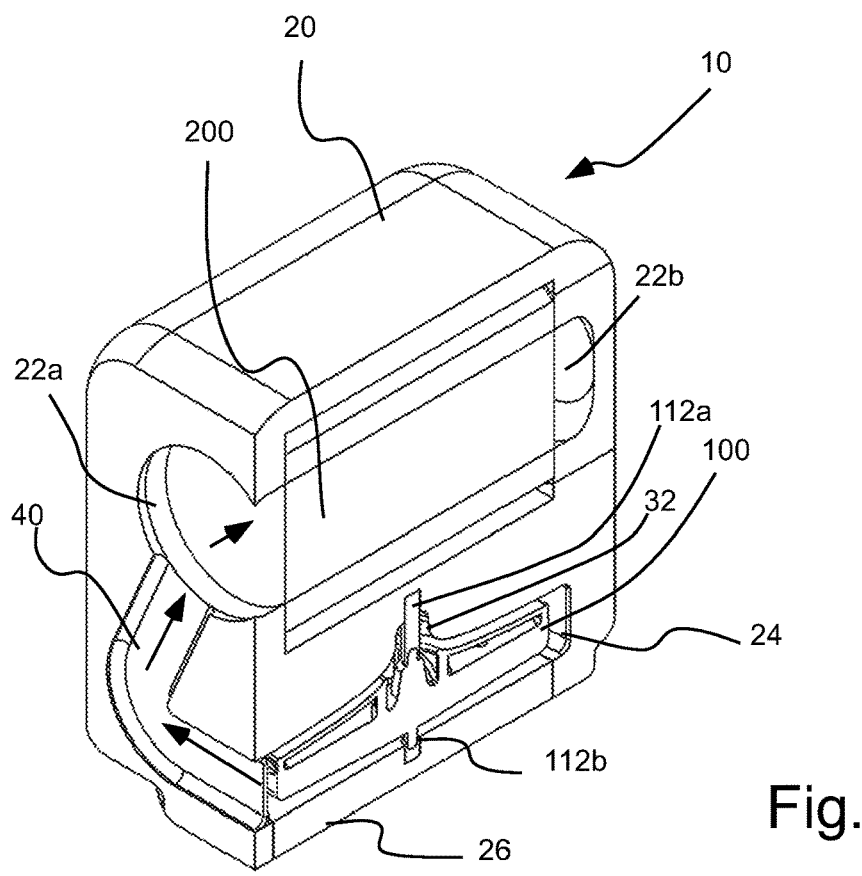
FIG. 1B illustrates a perspective, cutaway view of the system of FIG. 1A showing blood flow from the impeller to the fiber bundle.
Figure 4A:
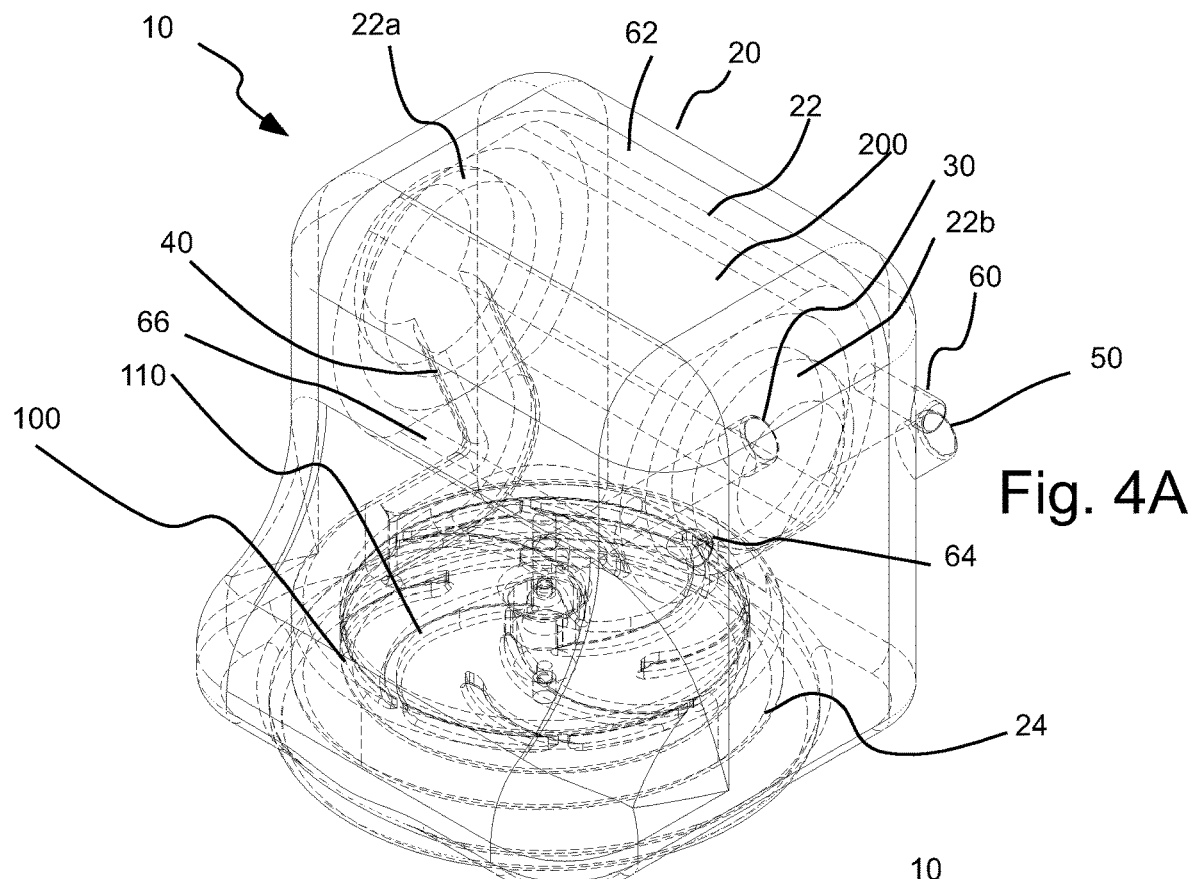
FIG. 4A illustrates a perspective, hidden line view of the system of FIG. 1A.
Figure 4B:
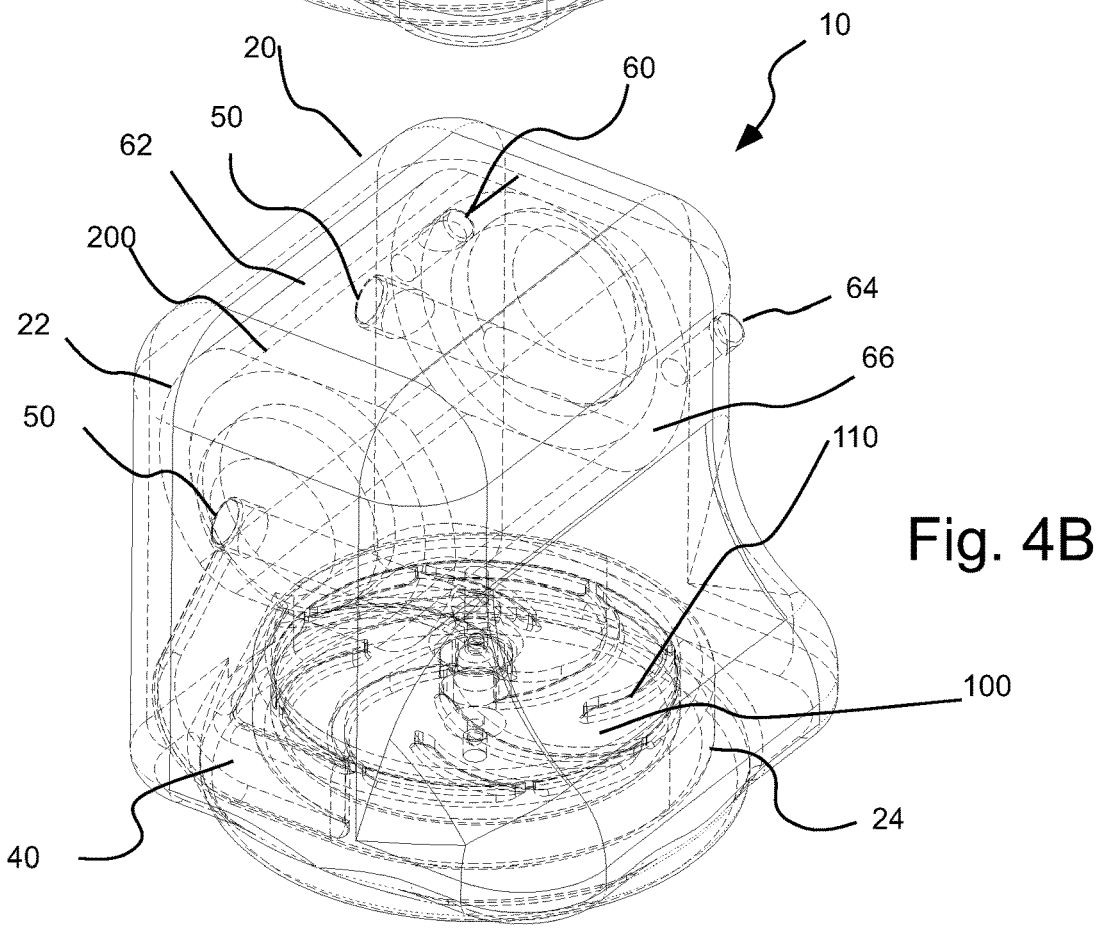
FIG. 4B illustrates another perspective, hidden line view of the system of FIG. 1A.
Figure 5A:
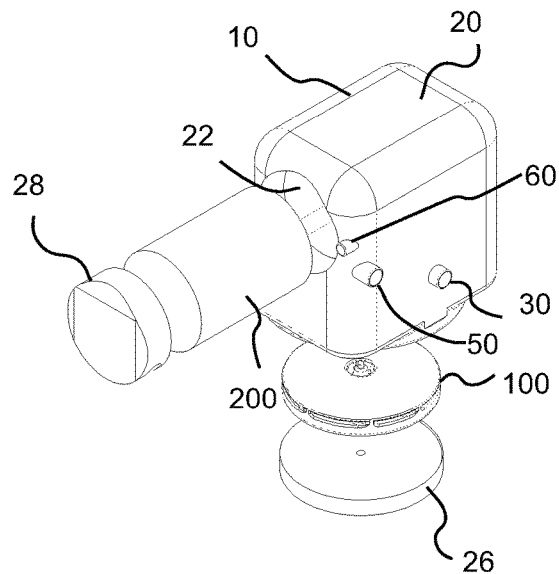
FIG. 5A illustrates a perspective disassembled or exploded view of the system of FIG. 1A.
Figure 5B:
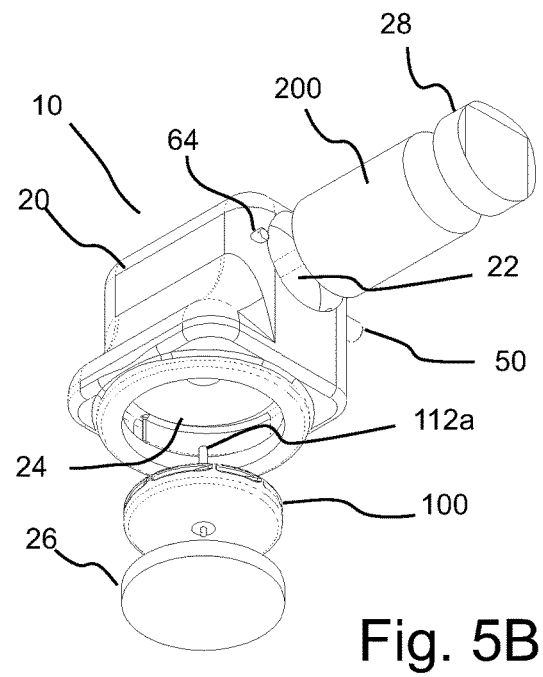
FIG. 5B illustrates another perspective disassembled or exploded view of the system of FIG. 1A.
Figure 6A:
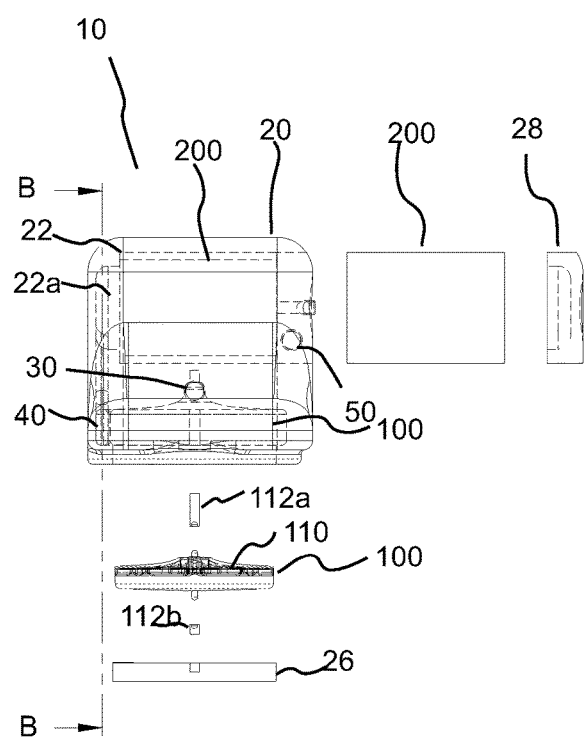
FIG. 6A illustrates a front, hidden line, disassembled or exploded view of the system of FIG. 1A.
Figure 6B:
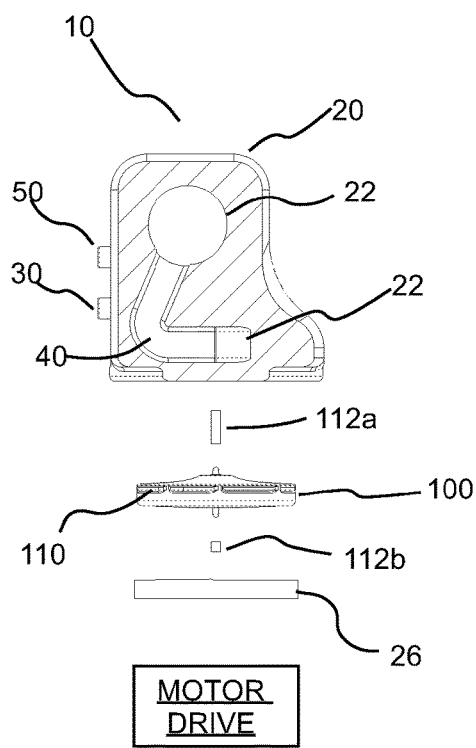
FIG. 6B illustrates a side, partially cross-sectional (section B-B with reference to FIG. 6A), disassembled or exploded view of the system of FIG. 1A.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "an impeller" includes a plurality of such impellers and equivalents thereof known to those skilled in the art, and so forth, and reference to "the impeller" is a reference to one or more such impellers and equivalents thereof known to those skilled in the art, and so forth. Recitation of ranges of values herein are merely intended to serve as a shorthand method of referring individually to each separate value falling within the range. Unless otherwise indicated herein, each separate value and intermediate ranges are incorporated into the specification as if individually recited herein. All methods described herein can be performed in any suitable order unless otherwise indicated herein otherwise clearly contraindicated by the text.

In a number of embodiments, extracorporeal/paracorporeal ambulatory assist lung system hereof provide advantages in gas transfer efficiency and biocompatibility. The systems hereof may, for example, be designed for either central and/or peripheral cannulation and respiratory support of, for example, 1-3 months duration before device change-out may be required. Systems hereof are, for example, amenable to patients suffering from severe acute respiratory failure (ARDS) to chronic patients suffering from COPD or severe pulmonary hypertension (PH). Paracorporeal device or systems are extracorporeal devices generally located immediately adjacent to the body during use. In other words, paracorporeal devices or systems are "wearable" or ambulatory devices or systems. The systems hereof are well suited for paracorporeal/ambulatory use as well as use as generally stationary extracorporeal systems.

The system hereof are less cumbersome than ambulatory ECMO systems currently under development while providing for increased ambulatory respiratory assist. In a number of embodiments, systems hereof provide a highly integrated blood pump and lung, in which a pump mechanism such as an impeller pressurizes blood for flow through hollow gas permeable fibers (sometimes referred to herein as a fiber bundle). Systems hereof may, for example, be designed to be worn in a holster or vest paracorporeally. Systems hereof may, for example, provide for increased average or mean velocity through the fiber bundle as compared to other devices, which enhances gas exchange.

In a number of embodiments of a system 10 hereof as illustrated in FIGS. 1A through 7B, system 10 includes a housing 20. Housing 20 brings all the components of system 10 together in an integrated manner such that a pressurizing system and the fiber bundle are encompassed within a relatively small form factor. Further system 10 provides for efficient and significant gas transfer rate without inducing significant blood damage.

Housing 20 includes a first or fiber bundle compartment 22 which houses a fiber bundle 200 and provides a gas pathway designed to uniformly perfuse the gas side of fiber bundle 200 with a sweep gas which may be oxygen or a gas mixture including oxygen. In a number of embodiment, the dimensions of housing 20 were no more than 12.7 cm (5 inches) in height, no more than 12.7 cm (5 inches) in width, and no more than 12.7 cm (5 inches) in length. This form factor may be further reduced by increasing pumping efficiency (for example, by further optimizing impeller design).

In that regard, pressurizing mechanism such as a rotating element or an impeller 100 may be positioned within a second, pressurizing or pumping (stator) compartment 24 of housing 20. In the illustrated embodiment, pumping compartment was formed as an impeller stator, volute compartment 24, which was formed integrally or monolithically with the remainder of housing 20. Impeller volute compartment 24 houses impeller 100 and may be designed in accordance with traditional pump theory to maximize the pumping efficiency of impeller 100. Impeller 100 fits within impeller volute compartment 24 of housing 20.

The stator section of a centrifugal pump, after flow exits the impeller, is usually either a diffuser or a volute. The purpose of each of these two stator types is to efficiently diffuse velocity energy into pressure. Diffusers are characterized by a plurality of radially symmetric diffusing passageways surrounding the impeller. Either a volute-shaped or annular collector is used in tandem with the diffuser. Volutes are characterized by one or more scroll-shaped diffusing passageways (one in a number of embodiments hereof), depending on the pump configuration. A volute hereof receives fluid being pumped by the impeller, slowing down the fluid's flow rate and converting kinetic energy into pressure. The volute curves and increases in area as it approaches the discharge port.

In a number of embodiments, impeller 100 was partially magnetically supported via one or more magnets position on or within impeller 100. Impeller 100, in the illustrated embodiment, is positioned within impeller volute compartment 24 such that the net hydrodynamic load on impeller 100 is upwards. Thus, the magnets used to support impeller 100 exerted a downward force on impeller 100. As, for example, discussed in PCT International Publication No. WO2014/085620, a magnet may be seated in a seating of impeller 100 and (in cooperation with another magnet which may be within or external to impeller volute compartment 24) is operable to apply force offset the combined hydrodynamic and coupling magnet forces, thereby minimizing the axial forces applied to the bearings, and improving overall system durability. Top and bottom pivot bearings 112a and 112b, respectively, may, for example, be ultra-high-molecular-weight polyurethane (UHMWPE) pivot and cup type bearings housed in a stainless steel shell, which maximizes their resistance to wear.

A lower, volute compartment lid or closure 26 (see, for example, FIG. 5A) was sized to allow insertion of impeller 100 into impeller stator/volute compartment 24 of housing 20. Similarly, a fiber bundle lid or closure 28 was sized to allow insertion of fiber bundle 200 into fiber bundle compartment 22 of housing 20.

FIG. 2B illustrates fluid entry to fiber bundle 200, through a fluid/blood flow inlet 30 in housing 20. In that regard, a fluid such as blood is drawn into the central portion of impeller 100 and centrifugally spun outwards via impeller vanes 110 as indicated by the radially outward oriented arrows in FIG. 2B. Blood is then channeled to fiber bundle 200 as shown in, for example, FIG. 1B. As, for example, illustrated in FIG. 1B, a channel 40 extends the height (that is, the vertical dimension in the orientation of FIG. 3C) of impeller 100 to, for example, maximize washing on the underside of impeller 100, as this is a common area for thrombus deposition in pivot pumps. In the illustrated embodiment, channel 40 extends to the same height as impeller volute compartment 24 and extends generally tangentially therefrom (for example, within 5 degrees of tangentially therefrom). The channel cross section may, for example, be relatively narrow, to conserve cross sectional area between inlet 30 and channel 40. For example, inlet 30 in several embodiment was circular in cross section and with a diameter of 0.009529 m (⅜ inch), with a cross-sectional area of $7.097 \times 10^{-5}$ m$^2$ (0.11 in$^2$). The channel height is governed by the impeller thickness as described above and extends at least the thickness of impeller 100 (in several embodiments, a minimum of 0.0127 m (0.5 in) and up to 0.01905 m (0.75 in)). To conserve cross-sectional area of $7.097 \times 10^{-5}$ m$^2$ (0.11 in$^2$), the width of channel 40 is between 0.00381 m (0.15 in) and 0.005588 m (0.22 in).

Channel 40 further is integrated into housing 20 in a way that it does not further increase the form factor of fiber bundle 200. In the illustrated embodiment, channel 40 travels upward (in the orientation of the drawings) along a side wall of housing 20 and enters an inlet volume or manifold 22a of fiber bundle compartment 22 in a generally radial direction (as discussed further below). Channel 40 is angled as shown in FIG. 2C. As shown in the cross-sectional view of FIG. 2D, this angling of channel 40 allows it to fit within the diameter of impeller 100. Further, the rounded rectangular or stadium cross-sectional geometry of channel 40 (see, for example, FIG. 1C) allows for a thin or narrow profile such that channel 40 fits as part of the volute around impeller 100, also shown in FIG. 1D. As used herein, the term "rounded rectangular" refers to a rectangle having rounded corners. The term "stadium" is an oblong geometry formed by joining arcs or semicircles to opposite ends of a rectangle. In general, channel 40 has an aspect ratio (the ratio of width to height) less than 1, of less than 0.5 (wherein, the height is the vertical orientation of channel 40 as illustrated in FIG. 3C). Providing rounded or arced corners/ends in channel 40 assists in, for example, reducing or minimizing hemolysis and thrombosis.

In a number of embodiments, the blood enters fiber bundle 200 and passes around the hollow fibers thereof. After passing through fiber bundle 200, blood exits system 10 via an outlet volume or manifold 22b, which is in fluid connection with a blood/fluid flow outlet 50. As, for example, illustrated in FIGS. 3A and 3C, the liquid/fluid flow path is separated from the gas flow path through system 100 by abutment/sealing with housing 20 at the periphery of fiber bundle 200 at each end thereof.

The gas pathway in system 10 may, for example, be relatively simple. Gas flows in through a gas inlet port 60 into a channel 62 on one side of fiber bundle 200 and out through a gas outlet port 64 in fluid connection with a channel 66 on the other side of fiber bundle 200. Thus, gas flow through fiber bundle 200 in the average or bulk direction of the uppermost arrow in FIG. 2B. Channel 62 is the inlet to the gas pathway and channel 64 is the outlet. The sweep gas passes through 62 across the lumens of the fibers into 64. Channel 62 is sealed from channel 64, for example, by the contact between housing 20 and fiber bundle 200. In a number of embodiments, the width of channel 62 was approximately 0.25 inches. This width was chosen to assist in uniformly perfusing all of the fibers in fiber bundle 200. The direction of gas flow may, for example, be such that it is generally along the direction of gravity when system 10 is worn by the patient, so that any condensation that is built up will be cleared as a result of the effect of gravity.

Fiber bundle 200 was manufactured in accordance with methods described in PCT International Publication No. WO2014/085620, the disclosure of which is incorporated herein by reference. However, the diameter of fiber bundle 200 was smaller than the fiber bundles of PCT International Publication No. WO2014/085620. In that regard, the diameter was chosen based on the desired mean velocity of blood through fiber bundle 200. Based on the predetermined diameter and fiber density of fiber bundle 200, the number of sheets was chosen to obtain a desired surface area. Mean velocity, as used herein, is defined as flowrate through system 20 divided by the cross-sectional area of fiber bundle 200.

Polymethyl Pentene (PMP) fibers used in studies hereof had an outer diameter or OD of 380 micron and an inner diameter or ID of 180 micron. These fibers were manufactured as arrays, membranes or fabrics of hollow fibers, wherein a plurality of fibers are fabricates as an integral, generally planar array having generally the same fiber orientation. In forming fiber bundle 200, such arrays, membranes or fabrics are cut into sheets that were placed one on top of the other in stack of multiple layers (200 layers in several studied embodiments of fiber bundle 200) such that the overall surface area for gas exchange was maintained at, for example, ~0.65 m$^2$. The porosity of fiber bundle was maintained at 0.5. Upon formation, fiber bundle 200 had a diameter of 1.75 inches (0.44 meters) and a height of 3.15 inches (0.08 meters).

In a number of embodiments, fiber bundle 200 was a generally cylindrical bundle of hollow fiber membranes (for example, siloxane and heparin coated fiber arrays, membranes or fabrics as described above) stacked in layers at, for example, 5-15 degree angles to one another and aligned generally perpendicular to the principal direction of blood flow (that is, generally perpendicular to axis A of fiber bundle 200—see FIG. 3B)) to maximize gas exchange. In a number of representative studied embodiments, fiber bundle 200 was a generally cylindrical bundle of hollow fiber membranes stacked in layers at approximately 14 degree angles to one another. In that regard, the fibers were cut into round sheets and stacked at a 14 degree angle between adjacent sheets into a potting mold. The ends of the hollow fibers were potted into semi-circular gas manifold channels (gas inlet manifold channel 62 and gas outlet manifold channel 66). Polyurethane glue was injected into the mold by using centrifugal force generated by spinning the mold in a lathe. The polyurethane binds all the fibers into fiber bundle 200. The thickness of the potting glue was roughly 0.25 in and was chosen to provide adequate mechanical support.

Aligning the hollow fibers generally perpendicular (for example, within no more 5 degrees from perpendicular or within nor more than 2.5 degrees of perpendicular) to axis A can significantly decrease volume (that is, improve compactness) as compared to systems in which hollow fibers are generally parallel to the axis of the housing/blood flow.

In a number of embodiments, fiber bundle 200 was sealed to axially extending sealing sections formed on an inner wall of fiber bundle compartment 22 to form generally semi-circular manifolds. The sealing sections may, for example, extend radially inward to contact and form a sealing connection with fiber bundle 200. Two sealing section may be used to form generally semi-circular (that is, extending approximately 180 degrees) manifolds. Additional sealing sections may, for example, be used to create manifolds that extend around the inner circumference of fiber bundle compartment 22 less than 180 degrees.

Fiber bundle 200 may, for example, be wound and positioned within a four-piece reusable mold made from, for example, acetal (Delrin) for potting. During potting, two-part polyurethane adhesive (available from Cas Chem, of Bayonne, N.J.) is injected into the mold. The mold is then centrifuged to assure even distribution around the periphery without any voids. Once the adhesive has cured, the potted fibers are removed and trimmed. This procedure establishes a common gas pathway between all fibers.

As described above, the fibers used in the studies of system 10 were provided in array, fabric or membrane form. Other approaches to improving thromboresistance include the use of zwitterionic molecular species attached (for example, covalently) to the surface of the fibers without significantly affecting gas transport across the fiber surface. Furthermore, blood flow paths and patterns in system 10 may be optimized using for example computational fluid dynamics or CFD for improved hemocompatibility. The ultimate anticoagulation requirements for system 10 may also be further reduced because blood exiting system 10 flows through the patient's lungs, which can continue to act as a filter of small emboli.

As described above, blood enters system 10 through fluid flow inlet or blood flow inlet port 30 and is pumped by impeller 100. In a number of studied embodiments, impeller 100 was supported by two pivot bearings 112a and 112b mounted into housing 20 and aligned with the central axis of radial impeller 100. As known in the bearing arts, pivot bearings 112a and 112b may for example, include a rounded end that rotatable relative to a bearing cup (for example, similar to a ball and socket joint. The bearing cups may, for example, be formed from ultrahigh molecular weights polyethylene and are available, for example, from Modern Plastics of Shelton, Conn. The use of pivot bearings 112a and 112b eliminates the need for seals and bearings. The pivot bearing maintain impeller 100 axially and radially aligned within system 10. Also, secondary saline infusion used in some systems to beep blood from contacting friction/heat generating components are not required. Fresh blood enters system 10 and flows across pivot bearings 105, continually flushing the area with fresh fluid.

Magnetically suspended or levitated impellers without bearings may, for example, be used to further increase longevity. However, system 10, in a number of embodiments, may require periodic change-out (for example, every 1-3 months) of system 10 as a result of fouling in the lung compartment. A simpler and less complex approach of magnetic coupling of impeller 100, but not magnetic levitation, was chosen in a number of embodiments. In the illustrated embodiment, magnets 150, which are seated in seatings 160 (see FIG. 7C-7F) on rotating impeller 100 couple magnetically to rotating magnets on an external motor drive (shown schematically in FIG. 6B)) to maintain a hermetic seal. System 10 may, for example, be powered by one or more batteries 80. In the illustrated embodiment, 8 relatively small (0.5" diameter by 0.25" thick) magnets 150 are used as "coupling magnets" to maintain a magnetic couple between the motor drive and impeller 100. A larger, centrally positioned magnet 154 is used to stabilize the hydrodynamic force.

During operation, an oxygen-containing "sweep gas" (for example, oxygen) flows into gas inlet channel 62 via gas flow inlet 60 and is distributed through the lumens of the individual fiber membranes of fiber bundle 200. Oxygen ($O_2$) diffuses out of the fibers into the flowing blood (flowing around the fibers and generally perpendicular to the orientation thereof) as carbon dioxide ($CO_2$) diffuses from blood into the fibers and is carried by the sweep gas to outlet channel 66 and therethrough to gas flow outlet 64. As described above, the blood then leaves system 10 via blood flow outlet 50. Oxygen and carbon dioxide exit the lumens of the fibers into gas outlet channel 66. As, for example, illustrated in FIG. 3C, the ends of fiber bundle 200 contacts a first end of fiber bundle compartment 22 of housing 20 and form gas inlet channel 62 and gas outlet channel 66. Blood is thereby prevented from directly flowing into gas inlet channel 62 and/or gas outlet channel 66. The potting of fiber bundle 200 prevents blood flow flowing radially out of fiber bundle 200 and into gas inlet channel 62 and/or gas outlet channel 66.

Systems 10 used in studies hereof were not optimized. As further described below, optimization may be effected, for example, using a number of tools including CFD, bench testing and/or in vivo studies. Operating between 1200-2400 RPM, system 10 could deliver flows from 3.5 to 5.0 liters per minute or LPM while generating pressure heads from 250 to 350 mmHg. This dynamic range enables system 10 to be attached using peripheral and/or central placement modes using either access cannula or directly connecting grafts.

Figure 10A:
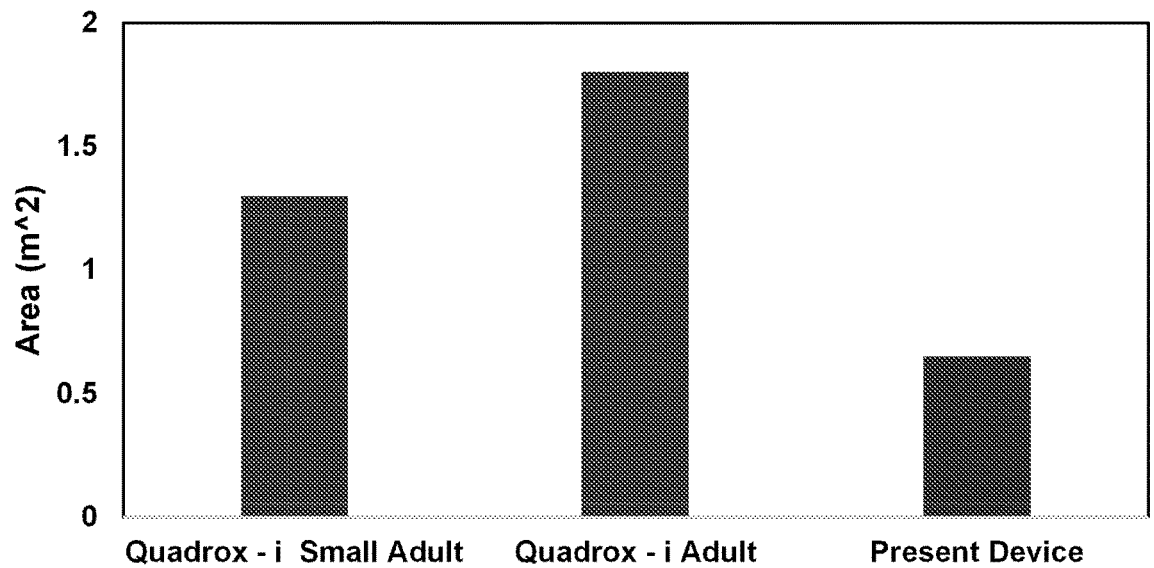
FIG. 10A illustrates a gas exchange surface of are of the system of FIG. 1A as compared to two other systems.
Figure 10B:
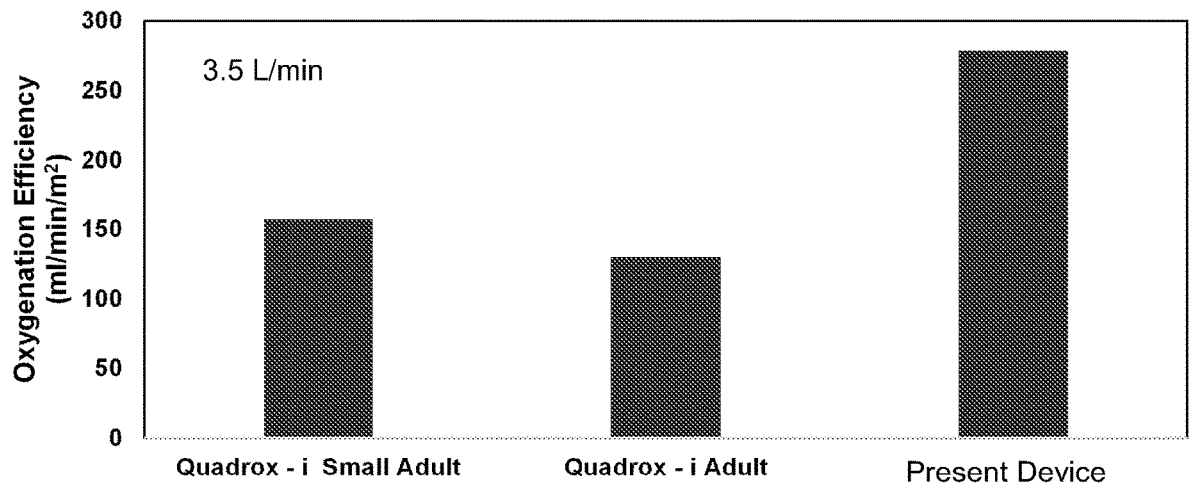
FIG. 10B illustrates a study of oxygenation efficiency at 3.5 L/min of the system of FIG. 1A as compared to two other systems.
Figure 11A:
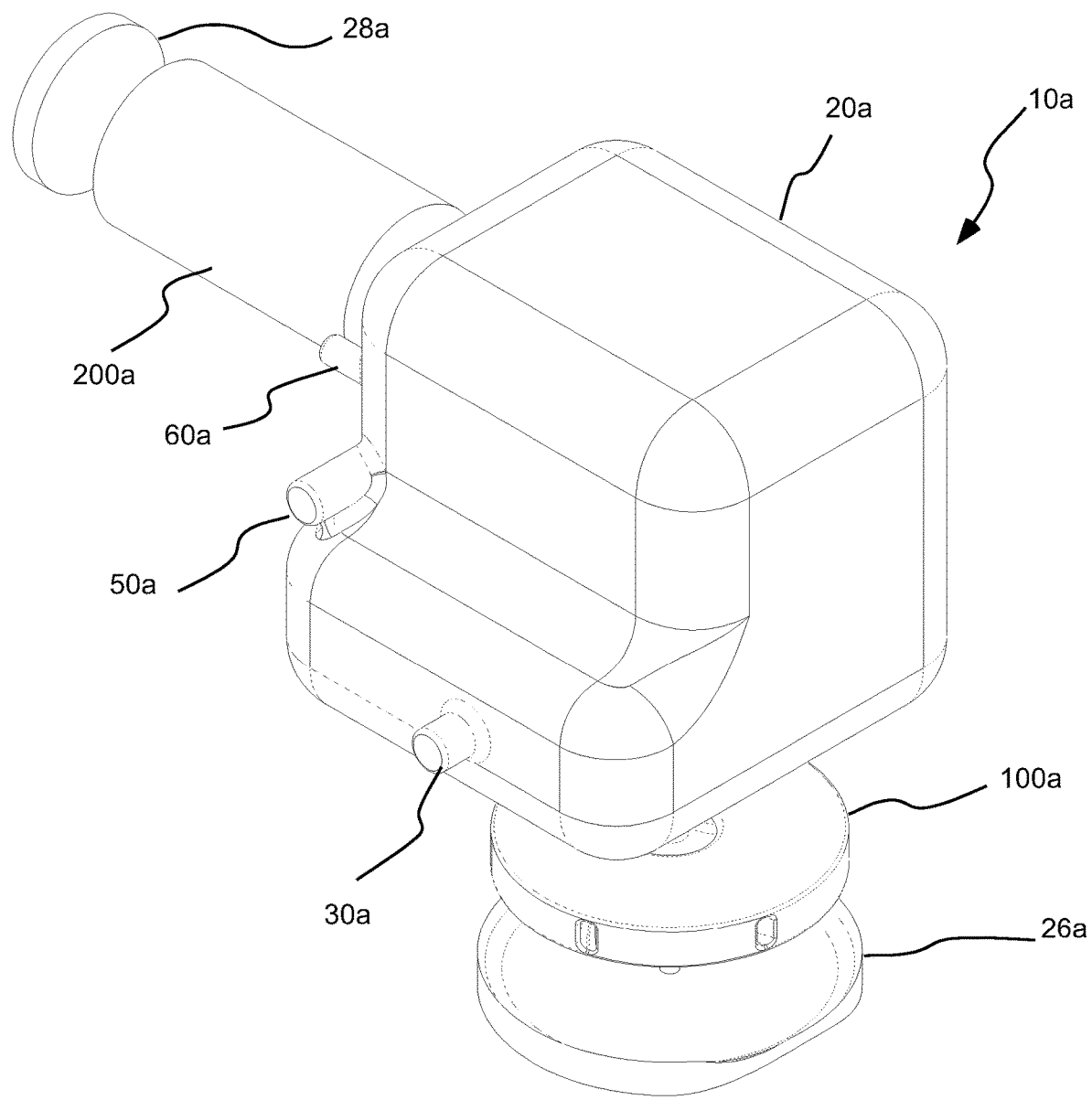
FIG. 11A illustrates a perspective view of another embodiment of a paracorporeal ambulatory assist lung apparatus, device or system hereof.
Figure 11B:
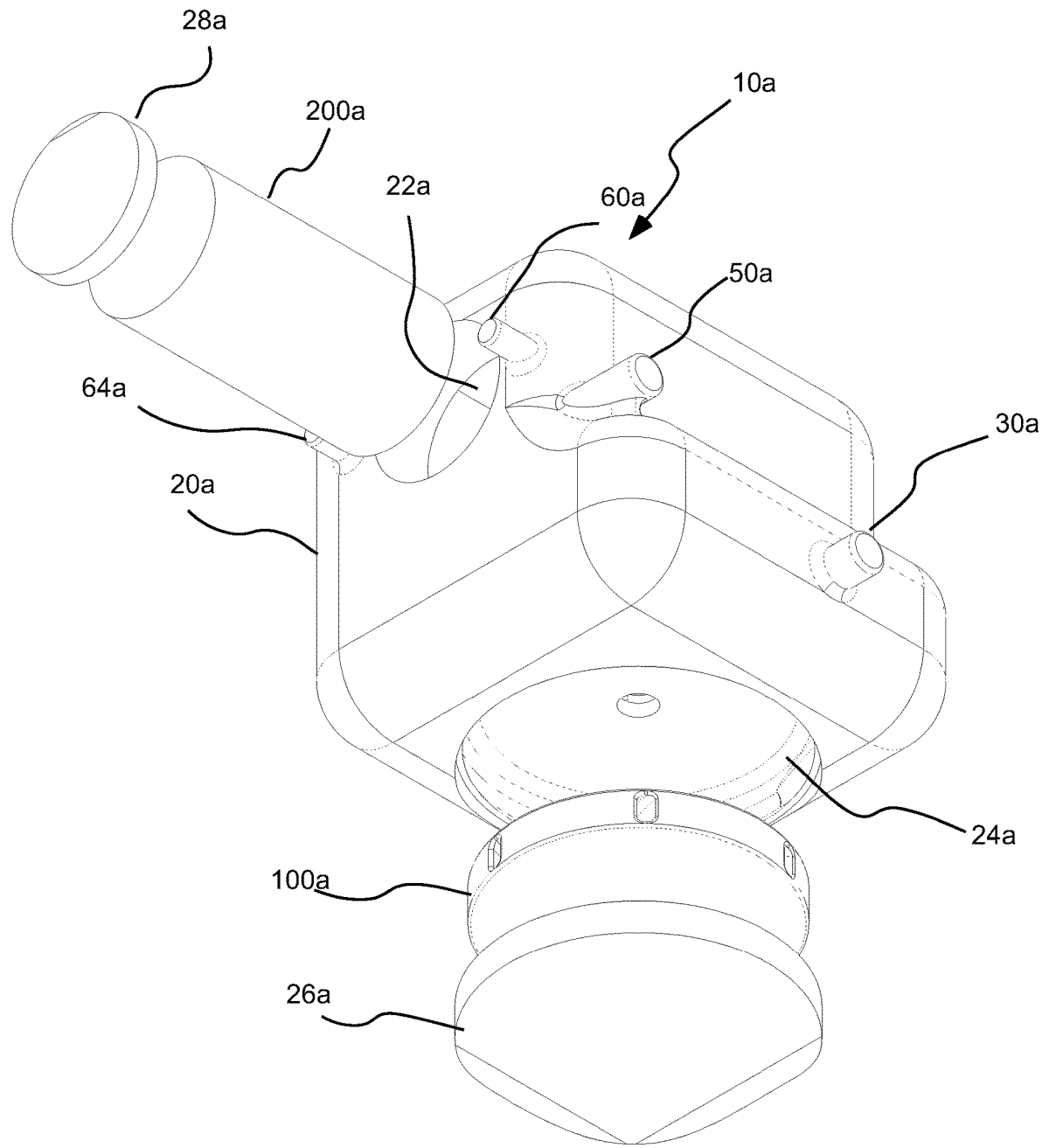
FIG. 11B illustrates another perspective view of the system of FIG. 11A.
Figure 12A:
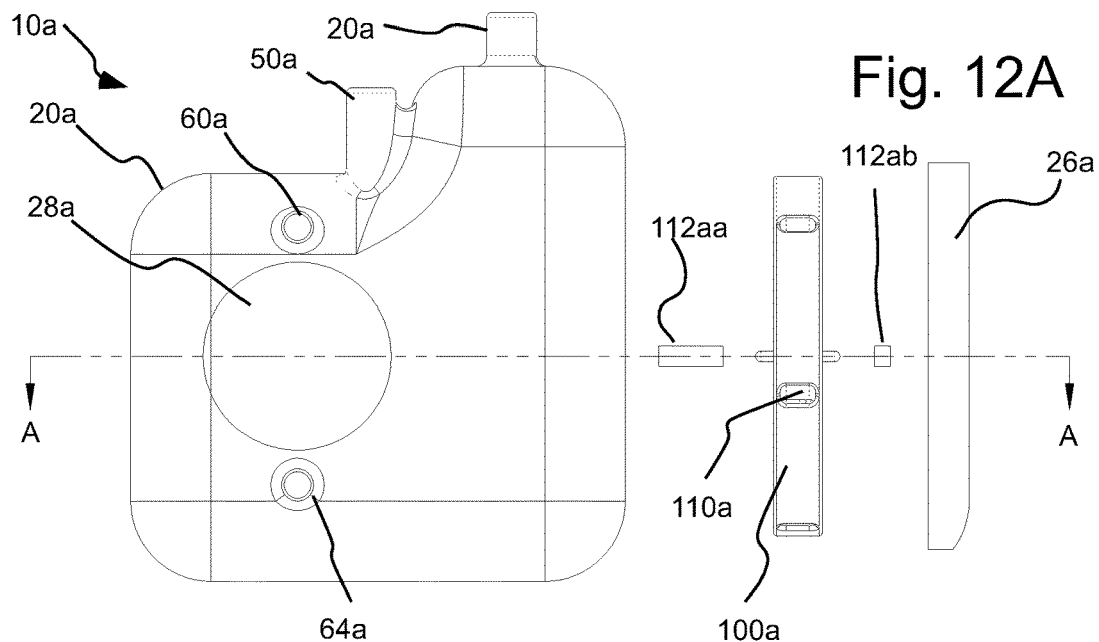
FIG. 12A illustrates a side of view the system of FIG. 11A.
Figure 12B:
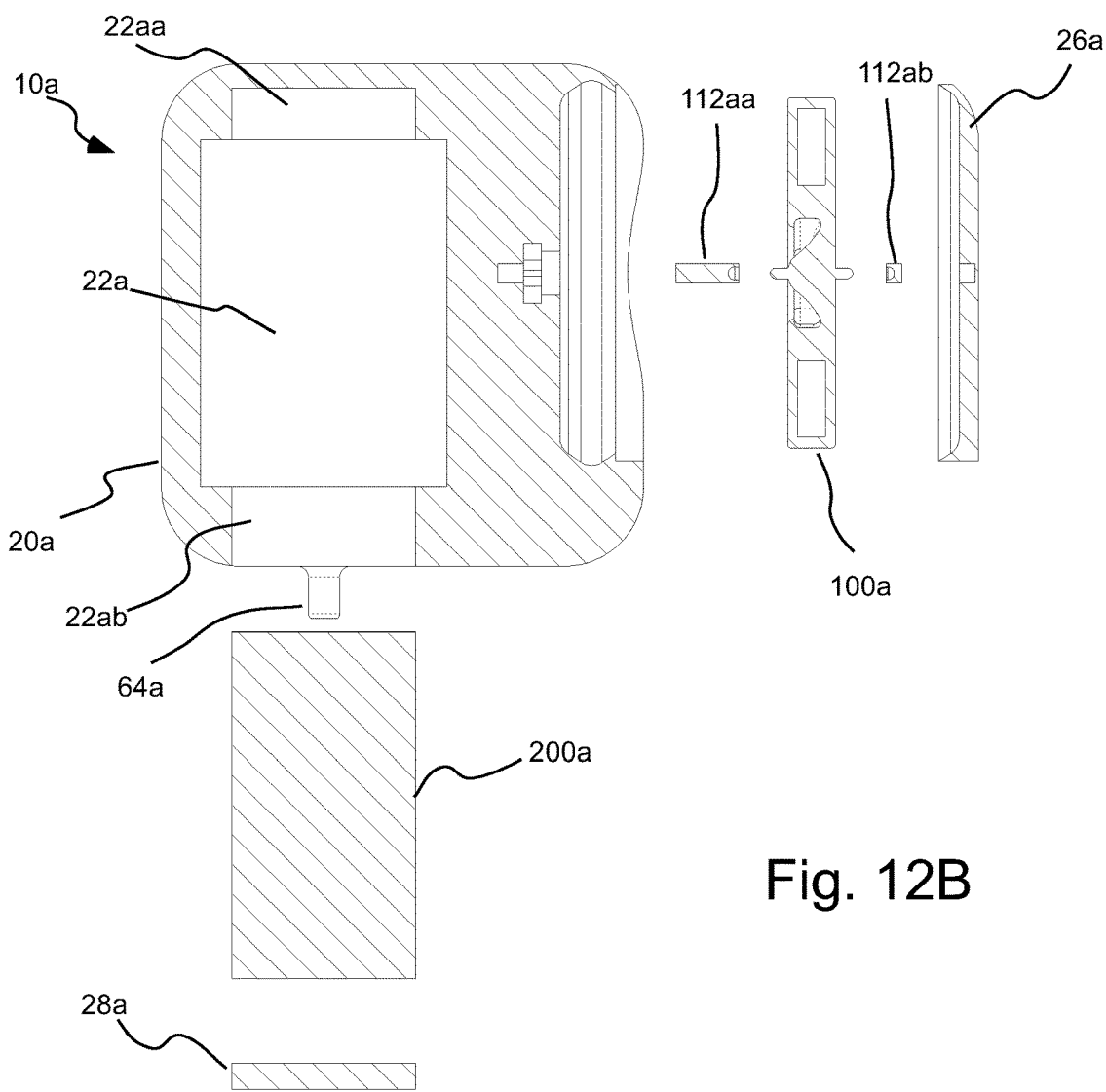
FIG. 12B illustrates a section A-A (see FIG. 12A) cross-sectional view of the system of FIG. 11A.
Figure 13:
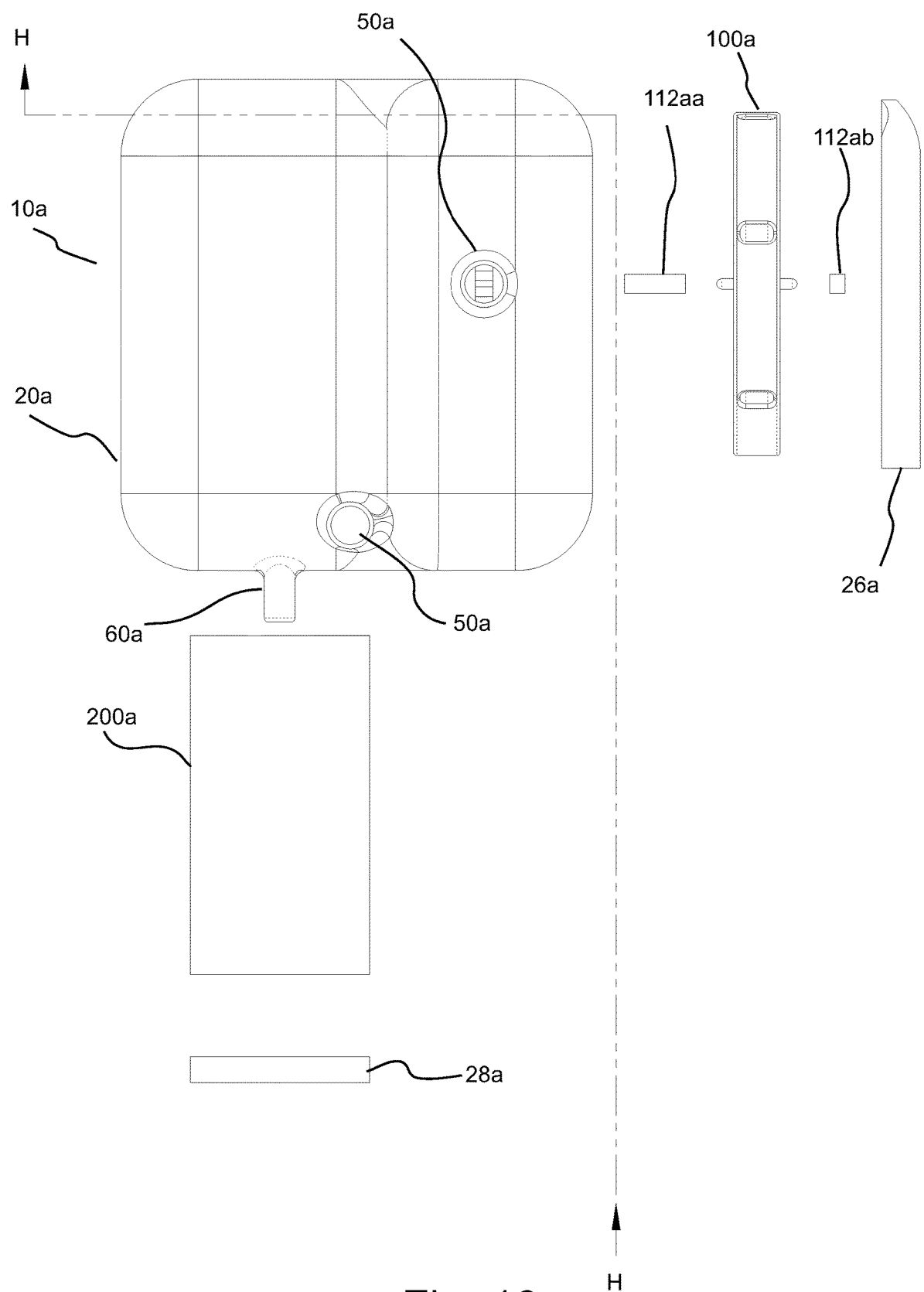
FIG. 13 illustrates another side view of the system of FIG. 11A.

Velocity in fiber bundle 200 governs the gas exchange efficiency as mass transfer in general is enhanced in high velocity environments. However, attaining relatively high velocities can induce hemolysis if not well controlled. In system 10, velocity is controlled by carefully specifying frontal/cross-sectional area of fiber bundle 200 to flow. This area is specified by the fiber bundle diameter. As described above, flow is normal to fibers. We have found that bundle diameters below 3 inches (or below 2.5 inches), provide increased efficiency. A generally cylindrical bundle having a diameter of 3 inches corresponds to a frontal area or cross-sectional area of 7.07 $in^2$, while a diameter of 2.5 inches corresponds to a frontal area or cross-sectional area of 4.9 $in^2$. In a number of embodiments, the diameter is no more than 2 inches (cross-sectional area of 3.14 $in^2$). In a number of studies, the diameter of fiber bundle 200 was 1.75 inch, corresponding to a frontal or cross-sectional area of 2.4 $in^2$, which provides an increased level of efficiency. As diameter is decreased, fewer fibers are able to fit in a single layer of fibers. Thus the number of fiber layers must be increased, which increases the height of a particular bundle, to achieve a predetermined rate of gas exchange. As such, a minimum height of 1.8 in was found to be required to provide sufficient number of fibers for a fiber bundle having a diameter of 2.5 inches and a cross-sectional area (or average cross-sectional area for an irregularly shaped bundle) of 4.9 $in^2$. System 10 achieves higher oxygenation through the shape of fiber bundle 100, which is longer and has a smaller diameter than, for example, the fiber bundle of the system of PCT International Publication No. WO2014/085620. This form increases the mean velocity of blood across the fibers to increase efficiency without needing active mixing as described in PCT International Publication No. WO2014/085620. By doing so, system 10 is able to achieve higher oxygenation per surface area than the other artificial lungs system as, for example, illustrated in FIGS. 10A and 10B. The systems hereof may be referred to as "passive" as there is no active mixing element adjacent to or in the vicinity of fiber bundle 200. Once again, increased efficiency is achieved via increased mean velocity of blood through fiber bundle 200.

Figure 8A:
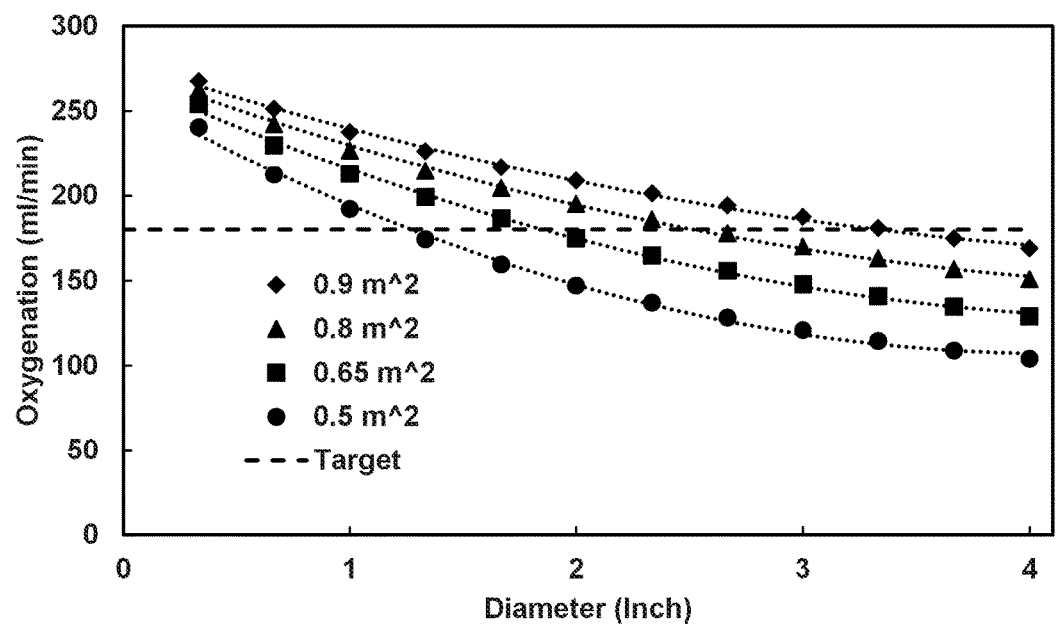
FIG. 8A illustrates a graph of oxygenation as a function of fiber bundle diameter.
Figure 8B:
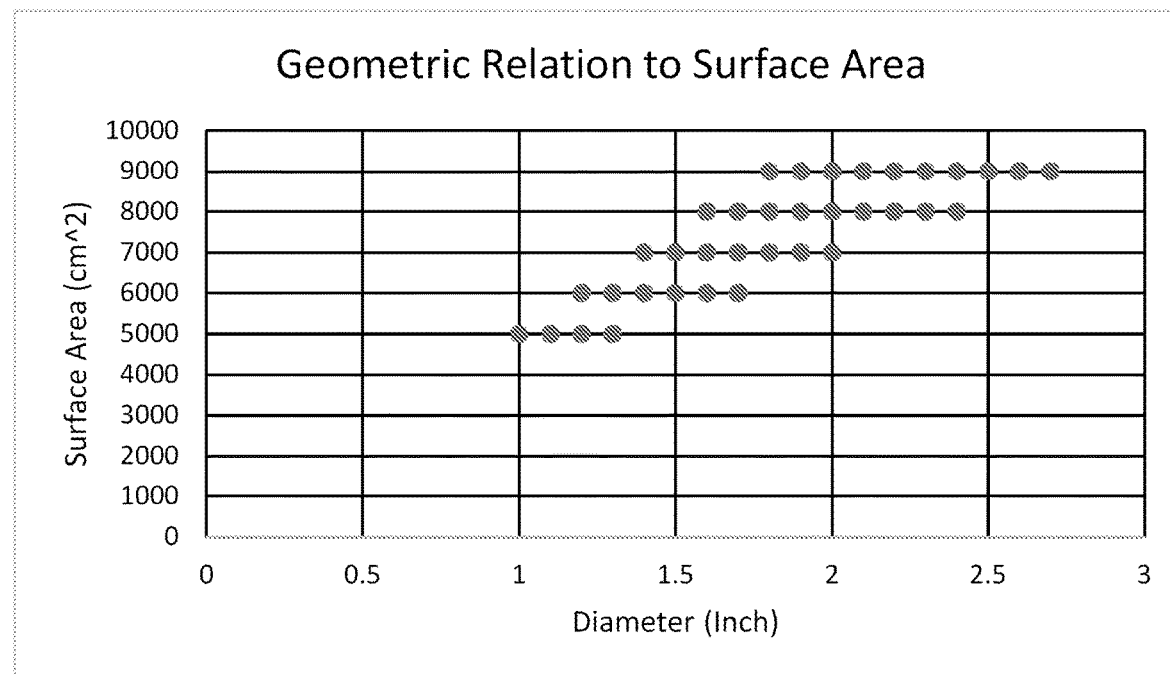
FIG. 8B illustrates a graph of form factors of fiber bundle (height, diameter) for a target oxygenation rate of between 160 ml/min to 180 ml/min.
Figure 8C:
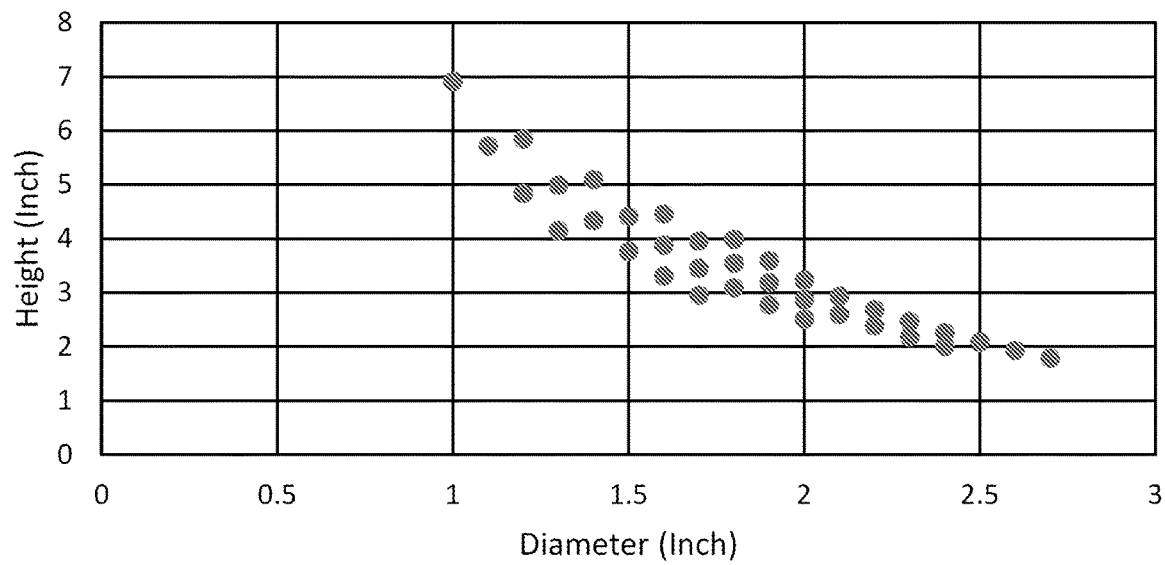
FIG. 8C illustrates a graph of form factors of fiber bundle (surface area, diameter) for a target oxygenation rate of between 160 ml/min to 180 ml/min.
Figure 8D:
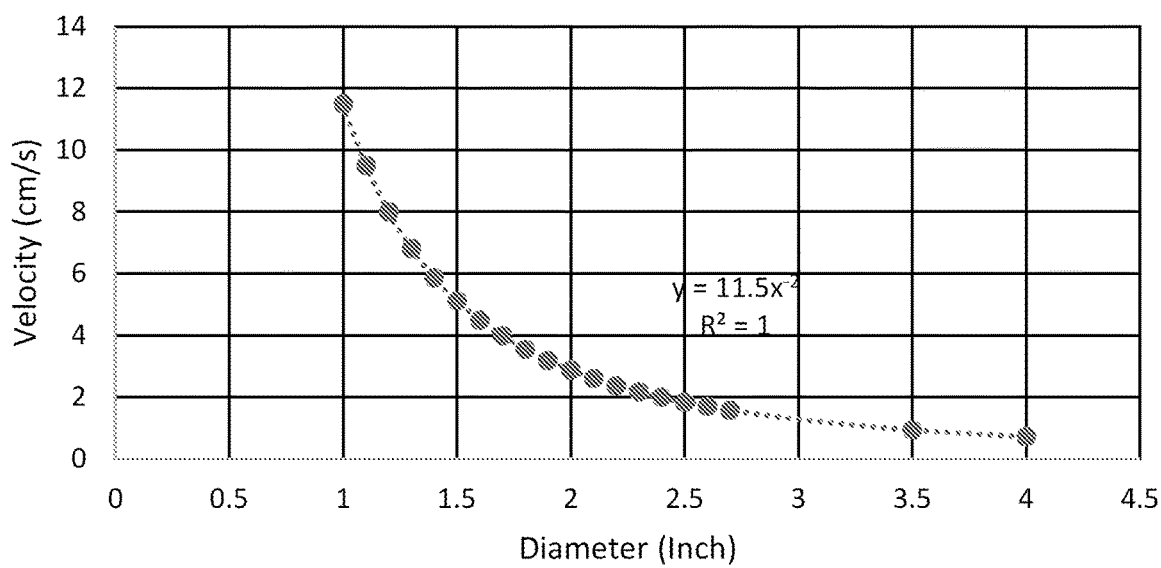
FIG. 8D illustrates the relationship between fiber bundle diameter and mean bundle velocity at a flow rate of 3.5 L/min.

Oxygenation as a function of diameter is shown in FIG. 8A, at a constant flowrate of 3.5 L/min. As diameter is reduced oxygenation increases. Further, the same level of gas exchange can be afforded by a lower surface area if diameter is sufficiently small. FIG. 8A was generated by applying principles of mass transfer to the fiber bundle geometry. The target oxygenation rate was between 160 ml/min to 180 ml/min as indicated by the dashed lines of FIG. 8A. As seen, many diameters and surface areas fall within this range. FIGS. 8B and 8C show form factors of fiber bundles (height, diameter, surface area) that fall within this range of oxygenation rate. The relationship between diameter and mean bundle velocity at 3.5 L/min is shown in FIG. 8D.

Normally, devices that have active mixing compromise on the level of blood damage as increasing blood velocity increases shear stress applied to the red blood cells. System 10 provides high control of velocity as it flows through the device. There is little or no mixing, which minimizes the turbulent flow in the fiber bundle and provides a smooth velocity profile. This allows one to, for example, increase velocity just enough to provide high efficiency without significantly damaging blood.

The orientation of the impeller with regard to the fiber bundle is also such that flow is carefully channeled from the impeller to the fiber bundle in a way that blood velocity is controlled, so as to prevent blood damage. We have studied such flow in CFD and have studied a number of different ways of channeling the flow to minimize or eliminate blood damage.

As described above, computational fluid dynamics (CFD) may be used to optimize the design and operational parameters of system 10 to meet requirements for blood pumping, gas exchange, priming volume, and form factor. CFD may be used to simulate blood flow and gas exchange. Upon validation, CFD may be incorporated into design optimization algorithms.

In that regard, CFD is an effective tool to streamline the design process of, for example, blood pumps and oxygenators. Developed and validated CFD simulations may be combined with formal design optimization to analyze and refine the design of system 10 and blood contacting components thereof (including, for example, the impeller region, other rotational surfaces, the fiber bundle, and connecting conduits). Optimization objectives may, for example, include maximizing gas exchange and minimizing the size of system 10. The objectives may have constraints imposed to ensure sufficient pumping capacity, while minimizing trauma to blood. Optimization provides an optimal set of design features such as impeller size and configuration, fiber bundle layout, active mixing surfaces and blood inlet and outlet ports.

CFD simulation may, for example, include a number of approaches. The laminar Navier-Stokes equations may, for example, be solved using commercial codes such as Fluent (v14, ANSYS Inc., Canonsburg, Pa.) and OpenFOAM (v3.0, OpenCFD Ltd. Bracknell, UK). Turbulence modeling in the rotor cavity region of the device may be applied as needed in regions of sufficient Reynolds number or in the event of a disparity between CFD predictions and flow visualization results. The fiber bundle may be modeled as a single lumped continuum (porous medium) using a modified Ergun equation to characterize the pressure losses and superficial velocity field therein. Oxygen and carbon dioxide exchange may, for example, be modeled using a convection-diffusion-source mass transfer approach of along with a nonlinear $O_2$ gas transfer model and a nonlinear $CO_2$ model. We developed a CFD model of complex blood flow and gas exchange in hollow fiber bundles which was experimentally validated. The CFD model is suitable to predict subtle features of impeller-generated flow patterns and the overall gas exchange.

Figure 9A:
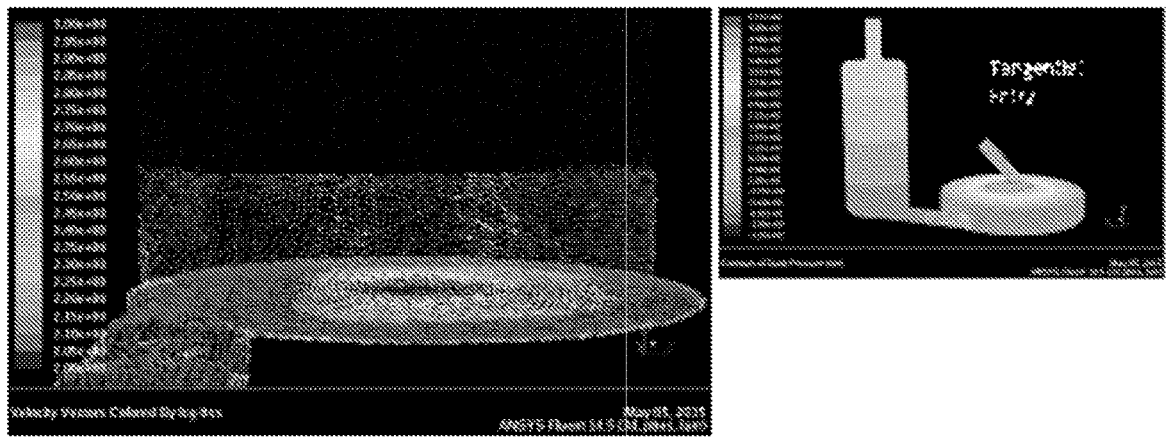
FIG. 9A illustrated a computational fluid dynamics or CFD model/study in which blood is introduced into an inlet side volume adjacent the fiber bundle in an orientation perpendicular to the orientation of flow through the fiber bundle and generally tangential to the inlet side volume.
Figure 9B:
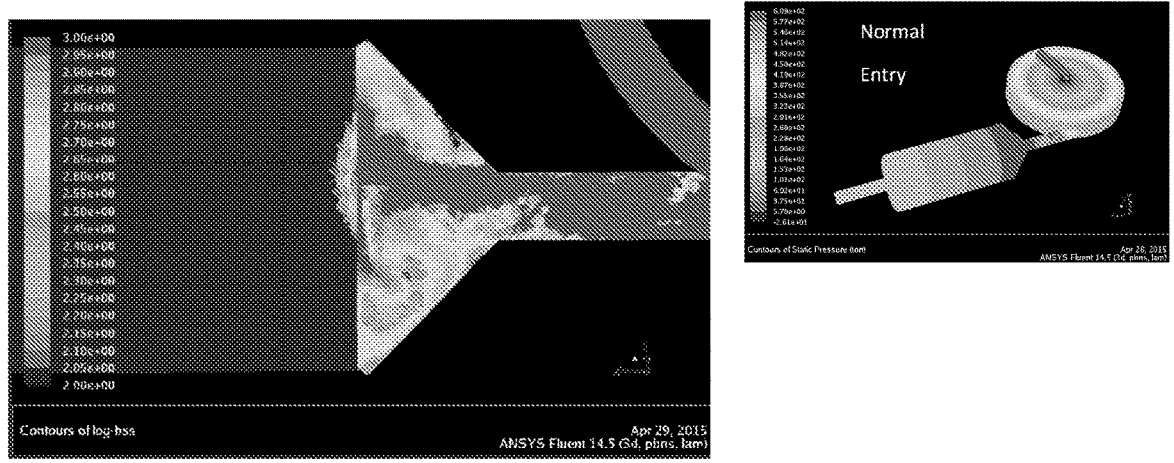
FIG. 9B illustrated a computational fluid dynamics or CFD model/study in which blood is introduced into an inlet side volume adjacent the fiber bundle in an orientation parallel to the orientation of flow through the fiber bundle and generally normal to the inlet side volume.
Figure 9C:
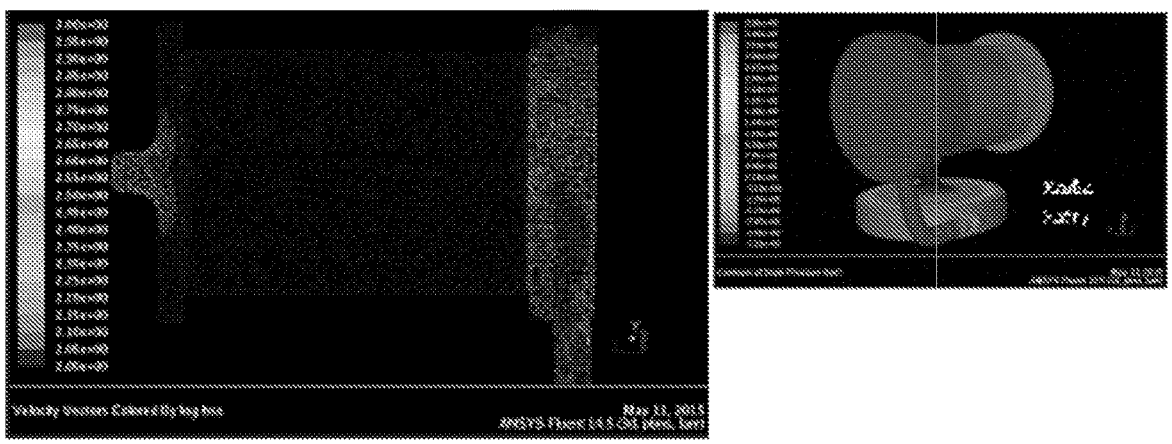
FIG. 9C illustrated a computational fluid dynamics or CFD model/study in which blood is introduced into an inlet side volume adjacent the fiber bundle in an orientation perpendicular to the orientation of flow through the fiber bundle and generally radially to the inlet side volume.

Preliminary CFD analysis of blood flow has been performed for system 10. One may computationally assess the hemocompatibility of system 10 using blood damage models for hemolysis, platelet activation, and thrombogenicity. A number of such models have been developed specifically for implementation with CFD. Plots were generated showing the log of shear stress in N/m 2. Stress values exceeding 1000 N/m 2 have been correlated to high hemolysis. It is desirable to minimize shear stress as blood enters fiber bundle 200. FIG. 9A illustrates a CFD model/study in which blood is introduced into inlet side volume 22a adjacent fiber bundle 200 in an orientation perpendicular to the orientation of flow through fiber bundle 200 (that is, perpendicular to axis A) and generally tangential to inlet side volume 22a. FIG. 9B illustrates a CFD model/study in which blood is introduced into inlet side volume 22a adjacent fiber bundle 200 in an orientation parallel to the orientation of flow through fiber bundle 200 (that is, parallel to axis A) and generally normal to inlet side volume 22a (that is, generally collinear with axis A). FIG. 9C illustrated a CFD model/study in which blood is introduced into inlet side volume 22a adjacent fiber bundle 200 in an orientation perpendicular to the orientation of flow through fiber bundle 200 (that is, perpendicular to axis A) and generally radially to inlet side volume 22A and to axis A. The tangential entry configuration of FIG. 9A does not induce high shear in fiber bundle 200, buy causes high levels of recirculation in inlet side volume 22a of fiber bundle compartment 22 before fluid enters fiber bundle 200 and can cause blood damage or thrombus formation. The latter two configurations show elevated shear levels in the first few fiber layers. FIG. 9B shows that shear stress in fibers where the fluid jet hits the bundle is in excess of 1000 $N/m^2$, making hemolysis a concern for this design. Once again, FIG. 9A has relatively lower shear stresses. However, in the plenum or inlet volume 22a, just before entering fiber bundle 200, a strong recirculating flow is seen. This recirculating flow has a stagnation point in the center (blue) area, which is known to have high propensity toward thrombus formation. FIG. 9C illustrates the radial inlet orientation that was chosen for system 20 as (1) fiber bundle 200 shows low shear stress and (2) strong recirculation regions are absent from the plenum or inlet volume 22a before fiber bundle 200.

Further CFD and engineering based optimization of flow channels was conducted on system 10 with the objective of mitigating "hot spots" for thrombus formation. The flow channels studied for optimization were (1) the inlet to the impeller, (2) the vanes of the impeller, (3) the outflow from the impeller and (4) the channel connecting the impeller to the fiber bundle. A system 10a hereof incorporating design characteristics determined in accordance with such further optimization studies is illustrated in FIGS. 11A through 14E. System 10a is similar in design and operation to system 10 and like component are numbered similarly with the addition of the designation "a" in the embodiment of system 10a. Like system 10, system 10a includes a housing 20a which brings all the components of system 10a together in an integrated manner such that a pressurizing system and the fiber bundle are encompassed within a relatively small form factor. System 10a also provides for efficient and significant gas transfer rate without inducing significant blood damage.

Housing 20a includes a first or fiber bundle compartment 22a which houses a fiber bundle 200a and provides a gas pathway designed to uniformly perfuse the gas side of fiber bundle 200a with a sweep gas as described in connection with system 20. As described above, in a number of embodiments, the dimensions of housing 20 were no more than 0.127 m (5 inches) in height, no more than 0.127 m (5 inches) in width, and no more than 0.127 m (5 inches) in length. A pressurizing mechanism such as a rotating element or an impeller 100a is positioned within a second, pressurizing or pumping (stator) compartment 24a of housing 20a. Pumping compartment 24a was formed as an impeller stator, volute compartment, which was formed integrally or monolithically with the remainder of housing 20a. Impeller volute compartment 24a houses impeller 100a.

Blood (or another fluid) enters impeller volute compartment 24a via an inlet 30a in housing 20a. As described above in connection with system 10a, a fluid such as blood is drawn into the central portion of impeller 100a and centrifugally spun outwards via impeller vanes 110a. Blood is then channeled to a fiber bundle 200a via channel 40a, which extends tangentially from impeller volute compartment 24a. Once again, the channel cross section is relatively narrow to conserve cross sectional area between inlet 30a and channel 40a. In the embodiment of system 10a, the diameter of inlet 30a transitions into a cardoidal shaped plenum which was 0.004318 m (0.170 in.) high as opposed to a straight cylindrical diameter of ⅜ in. as was the case for inlet 30. Inlet 30 diverts flow into impeller 100 via a smooth rounded 3D elbow 32 (see, for example, FIG. 14G) that results in some flow stagnation located aft of the impeller shaft. In contrast, inlet 30a diverts flow into the impeller 100a via the cardoidal shaped plenum 32a located at the terminal end of inlet 30a and above impeller 100a (see, for example, FIG. 14H). In a number of embodiments, plenum 32a had, for example, a cardioid shape. The purpose of the cardioid shape is to better distribute flow toward the aft side of the impeller shaft/pivot bearing 112a (which passes through plenum 32a) before its descending flow into the impeller region.

Inlet 30a also included an extension of the downward directed tubing deeper into the impeller region. The extension improves flow washing of the impeller shaft bearing 112a and decreases pre-swirl entering the rotor channels by redirecting the pressure-driven reverse flow in the top gap between impeller 100a and the shroud.

Figure 14A:
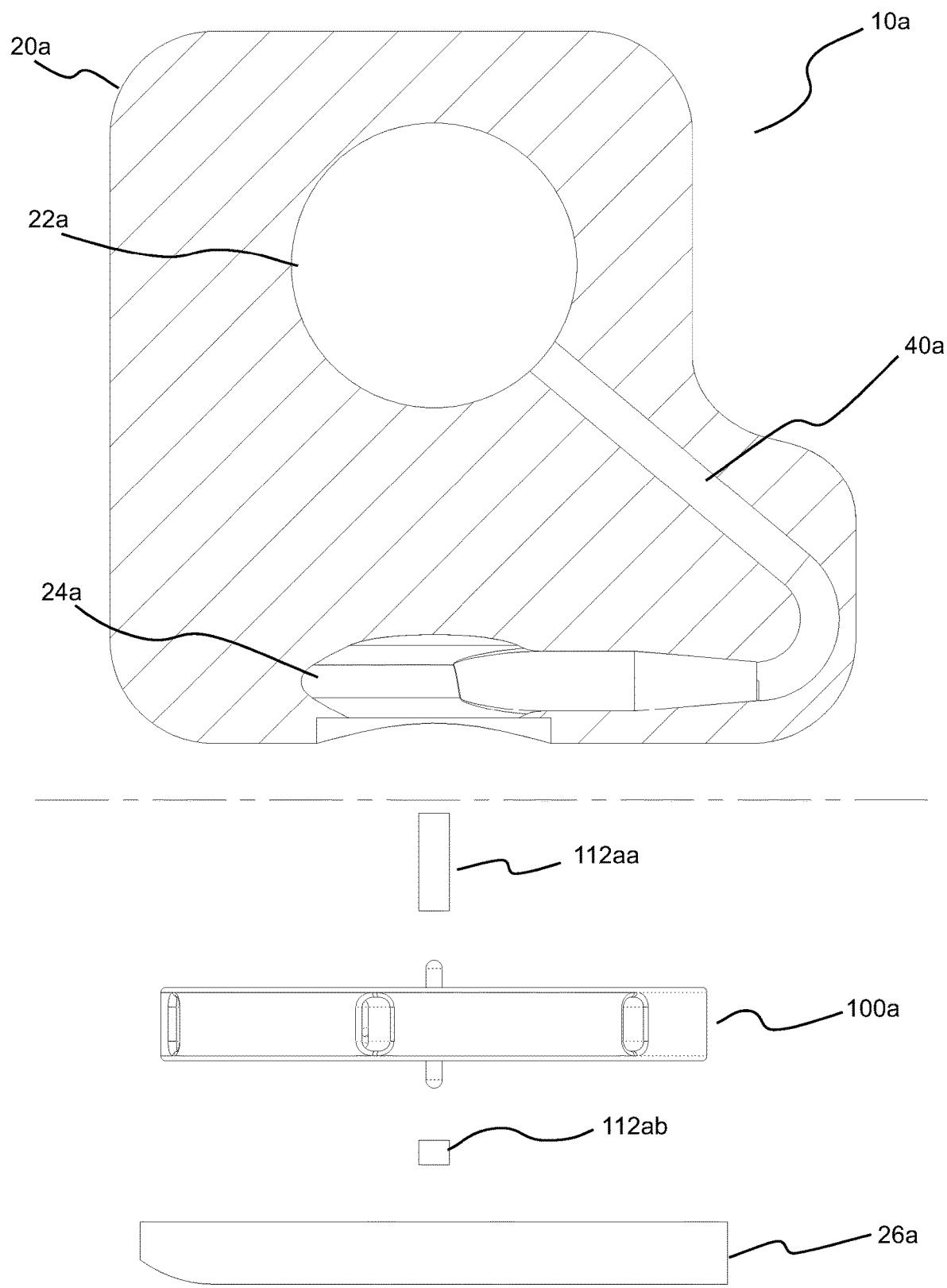
FIG. 14A illustrates a section H-H (see FIG. 13) cross-sectional view of the system of FIG. 11A.
Figure 14B:
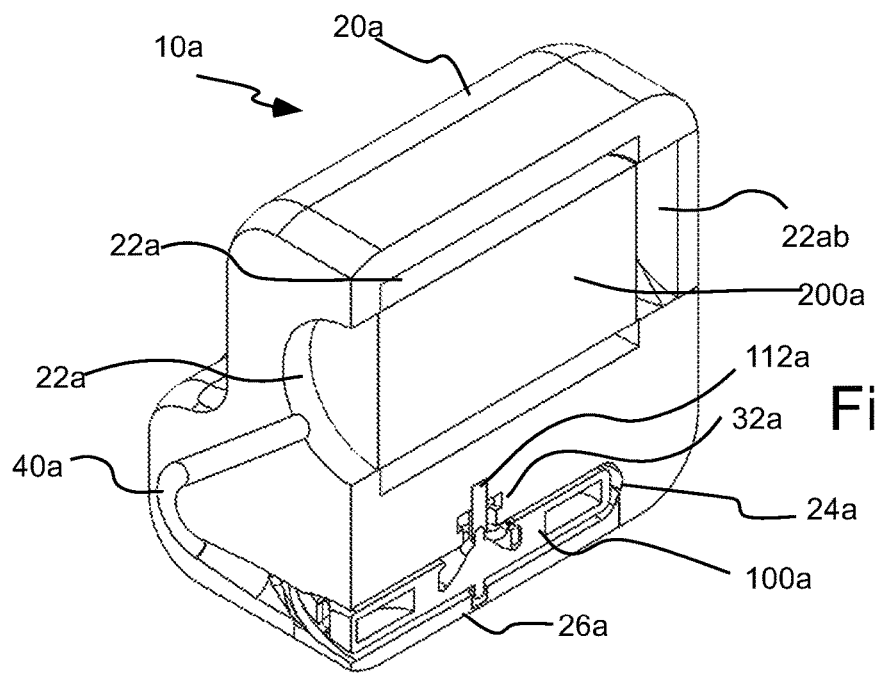
FIG. 14B illustrates a perspective cutaway view of the system of FIG. 11A.
Figure 14C:
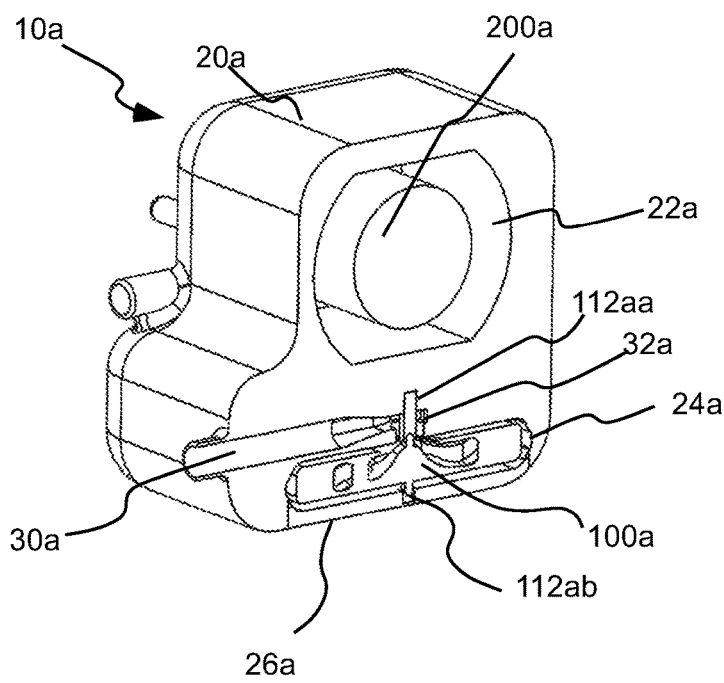
FIG. 14C illustrates another perspective cutaway view of the system of FIG. 11A.
Figure 14D:
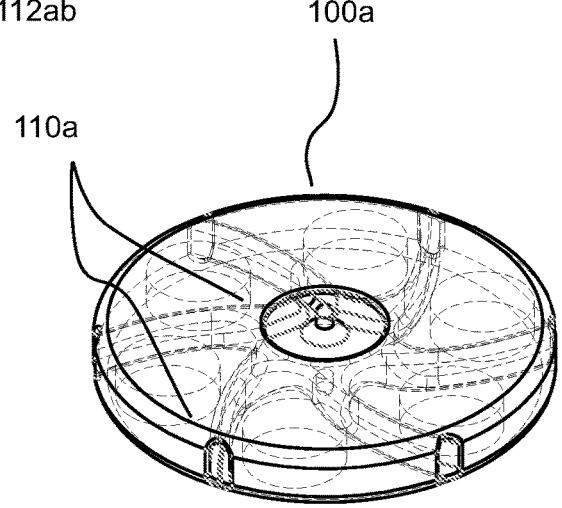
FIG. 14D illustrates a perspective hidden line view of the impeller of the system of FIG. 11A.
Figure 14E:
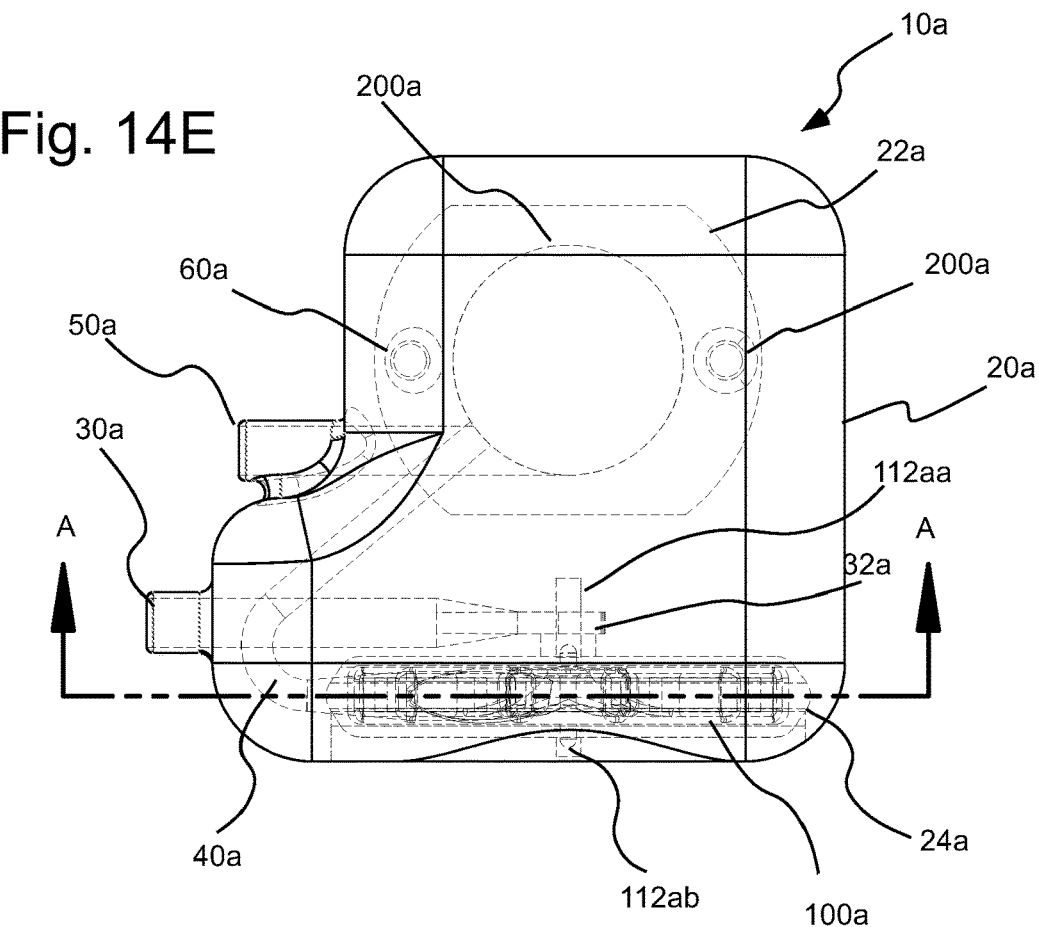
FIG. 14E illustrates a side, hidden line view of the system of FIG. 1A.
Figure 14F:
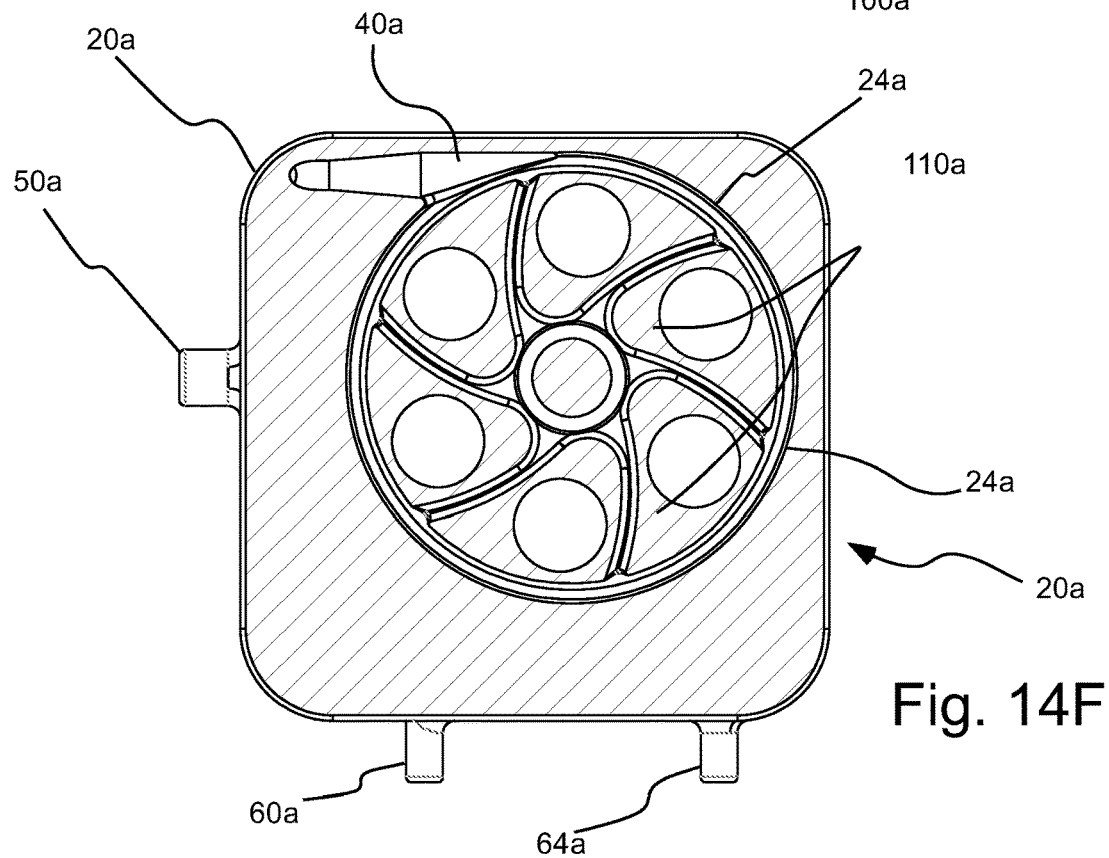
FIG. 14F illustrates a cross-sectional view (see section A-A of FIG. 14E) of the system of FIG. 11A further illustrating the impeller.
Figure 14G:
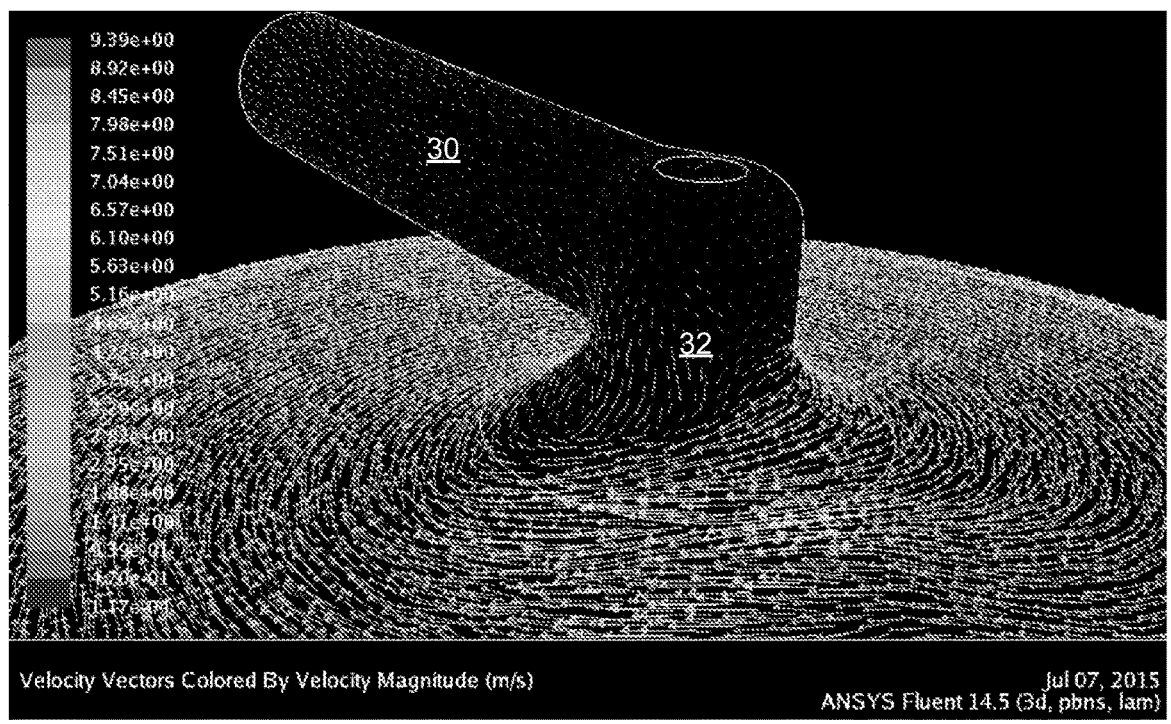
FIG. 14G illustrates a CFD study of blood flow from the blood flow inlet into the impeller of the system of FIG. 1A via a curved, 3-dimensional elbow conduit.
Figure 14H:
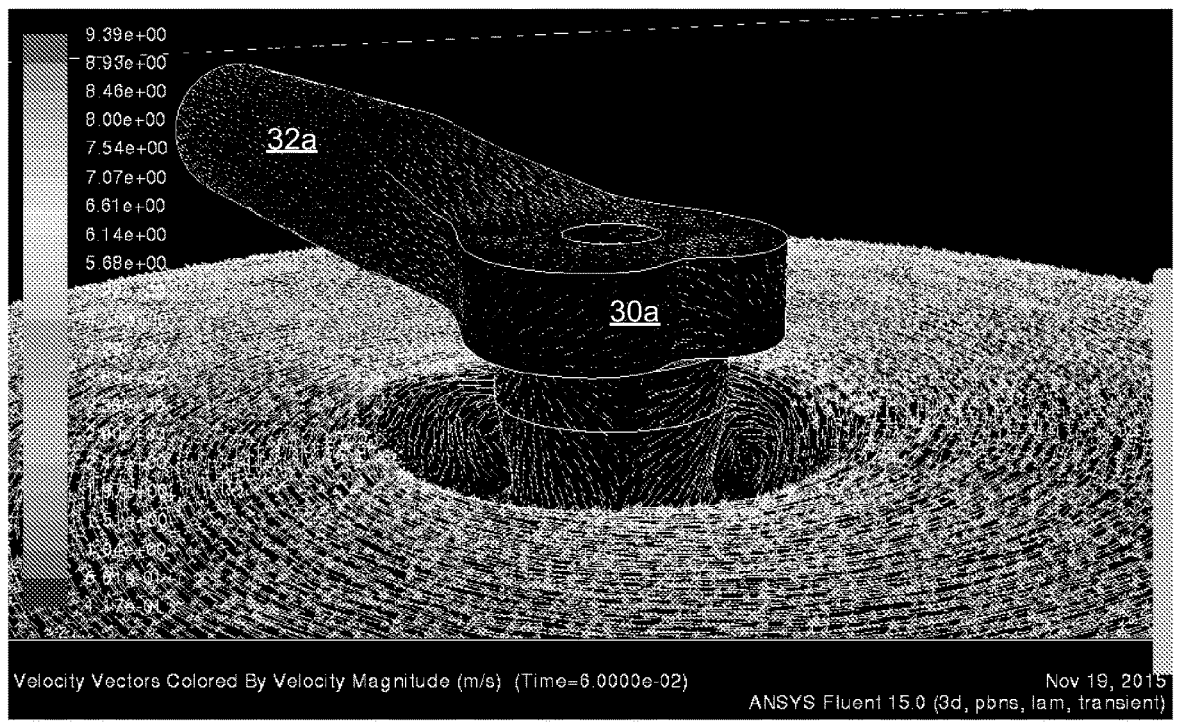
FIG. 14H illustrates a CFD study of blood flow from the blood flow inlet into the impeller of the system of FIG. 11A via a plenum.
Figure 14I:
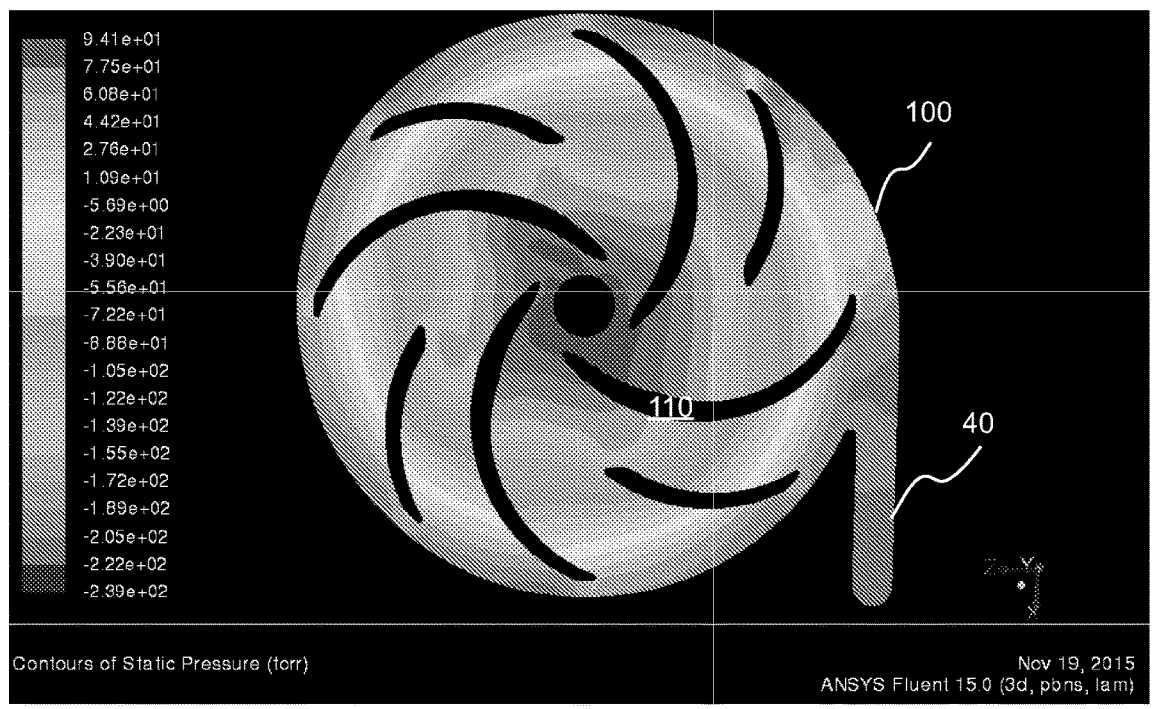
FIG. 14I illustrates a CFD study of blood flow within the impeller and pressurizing stator compartment of the system of FIG. 1A.
Figure 14J:
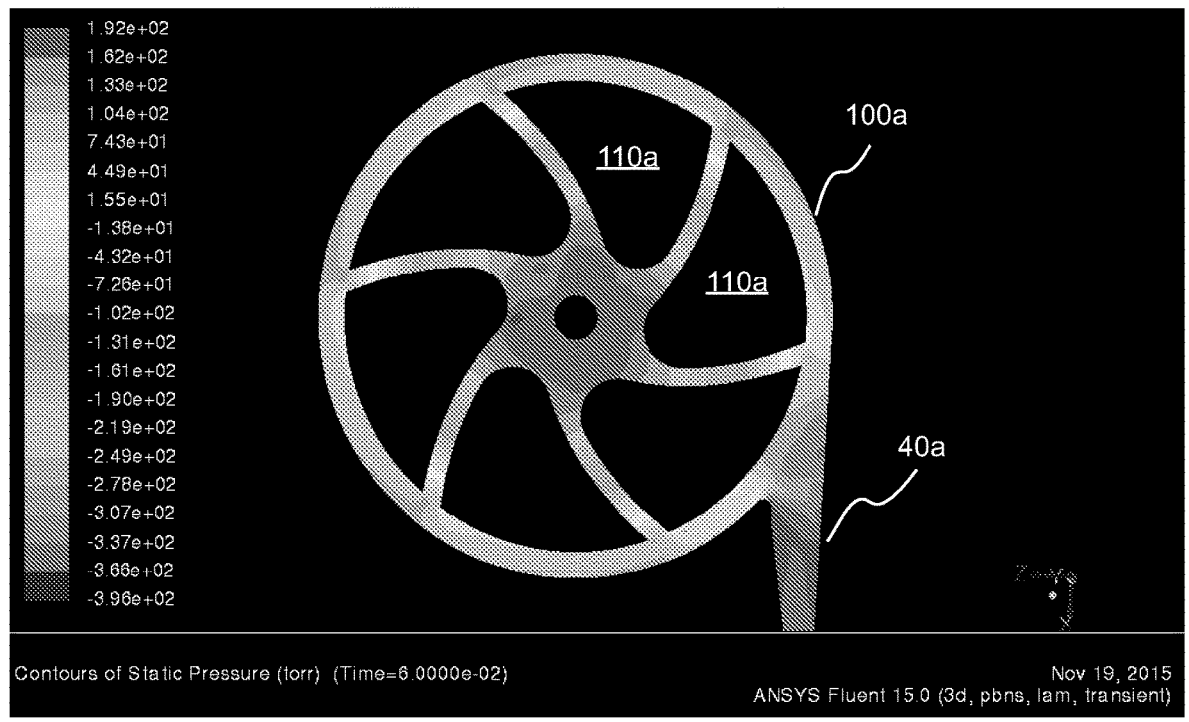
FIG. 14J illustrates a CFD study of blood flow within the impeller and pressurizing stator compartment of the system of FIG. 11A.
Figure 14K:
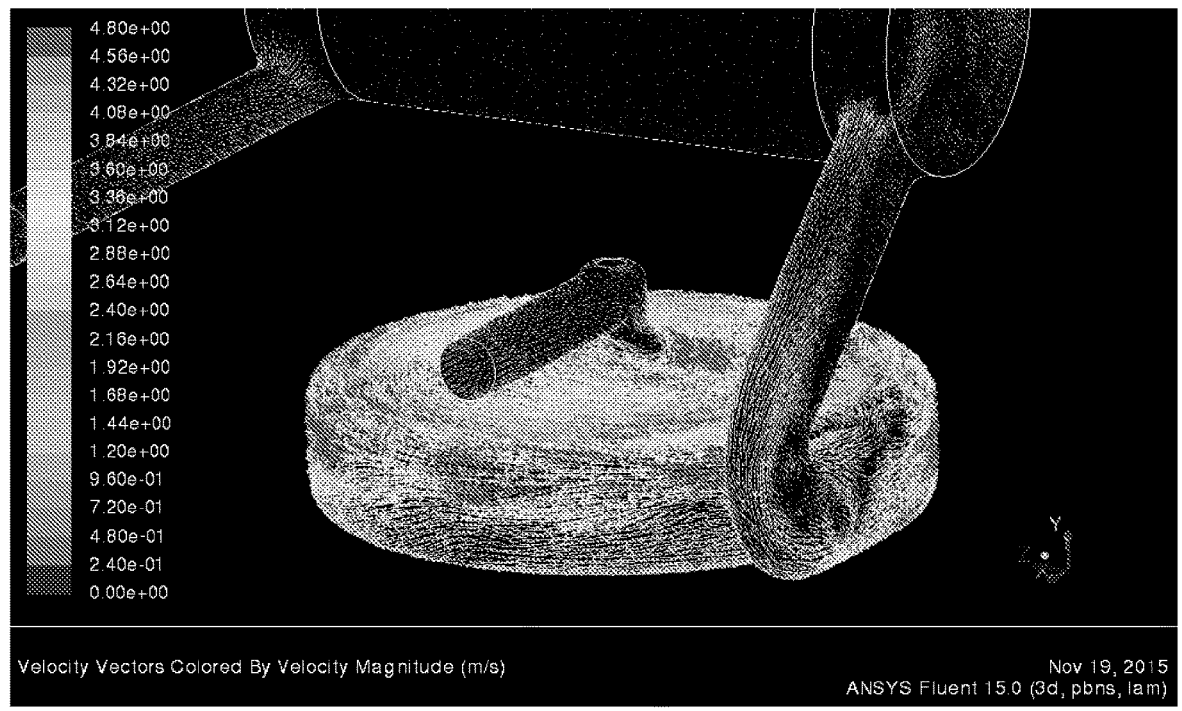
FIG. 14K illustrates a CFD study of blood flow within the fluid channel of the system of FIG. 1A.
Figure 14L:
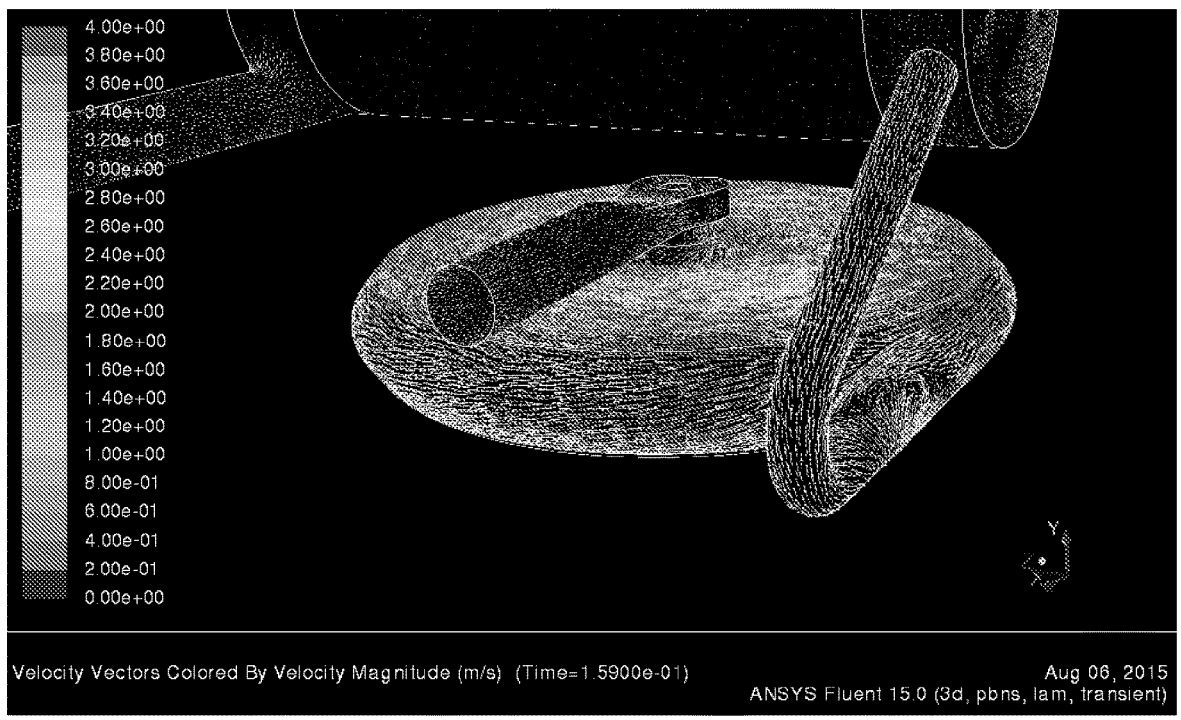
FIG. 14L illustrates a CFD study of blood flow within the fluid channel of the system of FIG. 11A.
Figure 14M:
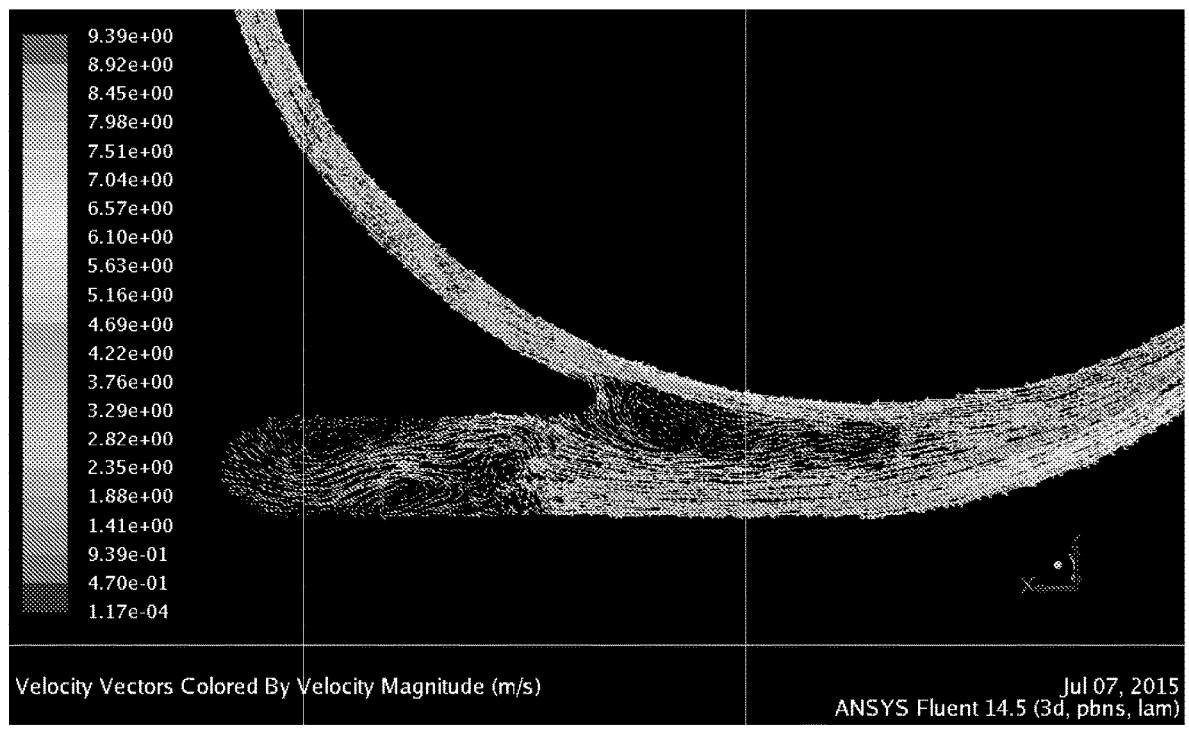
FIG. 14M illustrates a CFD study of blood flow in the vicinity of the cutwater of the pressurizing stator compartment/impeller volute of the system of FIG. 1A.
Figure 14N:
FIG. 14N illustrates a CFD study of blood flow in the vicinity of the cutwater of the pressurizing stator compartment/impeller volute of the system of FIG. 11A.

Flow channels through impeller 100a were narrowed as compared to flow channels through impeller 100, reducing the blade to blade distance as pictured in the cross section of impeller 100 set forth in FIG. 14F (as compared to impeller 100 illustrated in FIG. 2D). Impeller 100 includes traditional curved centrifugal pump blading 110 (illustrated as black voids in the CFD image of FIG. 14I) that are either open or closed with a shroud. The flow patterns in impeller 100 are chaotic. Impeller 100a includes curved flow channels instead of traditional blading. Conversely, one may consider blades 110a (illustrated as black voids in the CFD image of FIG. 14J) to be very thick with a large radius leading edge. The flow patterns in rotor 100a are much more controlled, resulting in improved hemodynamics, and reduce the potential of blood damage.

The outflow from impeller 100a was modified as compared to the outflow to impeller 100 by adjusting the 'cutwater' point distance (see, for example, FIG. 2D versus FIG. 14F) such that any flow reversal and leakage was mitigated as blood flowed from impeller 100a into channel 40a. In that regard, the relatively large cross-sectional areas of flow channel 40 lead to much flow and reversed flow (see the CFD image of FIG. 14k). Flow channel 40a is designed to converge the flow as it exits the pressurizing stator compartment/impeller volute 24a and then turn the flow via a smaller cross-sectional area channel to promote stronger flow attachment in the turn and up into fiber bundle manifold or plenum 22aa. As compared to channel 40, channel 40a was narrowed to a pipe of diameter of 0.0060452 m (0.238 in), increasing mean velocity therethrough to minimize any stagnation region (see the CFD image of FIG. 14L). CFD simulations indicated that these modifications yield improved hemocompatibility by mitigating thrombus formation in the flow channels. The combination of impeller 100a and outlet 40a produces better flow alignment and less flow separation at the pressurizing stator compartment/impeller volute 24a cutwater as illustrated in comparing FIG. 14M for system 10 and FIG. 14N of system 10a.

Similar to channel 40, channel 40a is integrated into housing 20a in a way that it does not further increase the form factor of fiber bundle 200a as described in connection with system 10a. In that regard, channel 40a travels upward (in the orientation of, for example, FIG. 14B, and along a curved or turned path) along a side wall of housing 20a and enters an inlet volume or manifold 22aa of fiber bundle compartment 22a in a generally radial direction. The passage of a fluid such a blood and gas through fiber bundle 200a of system 10a is similar to that described in connection with system 10.

Figure 15:
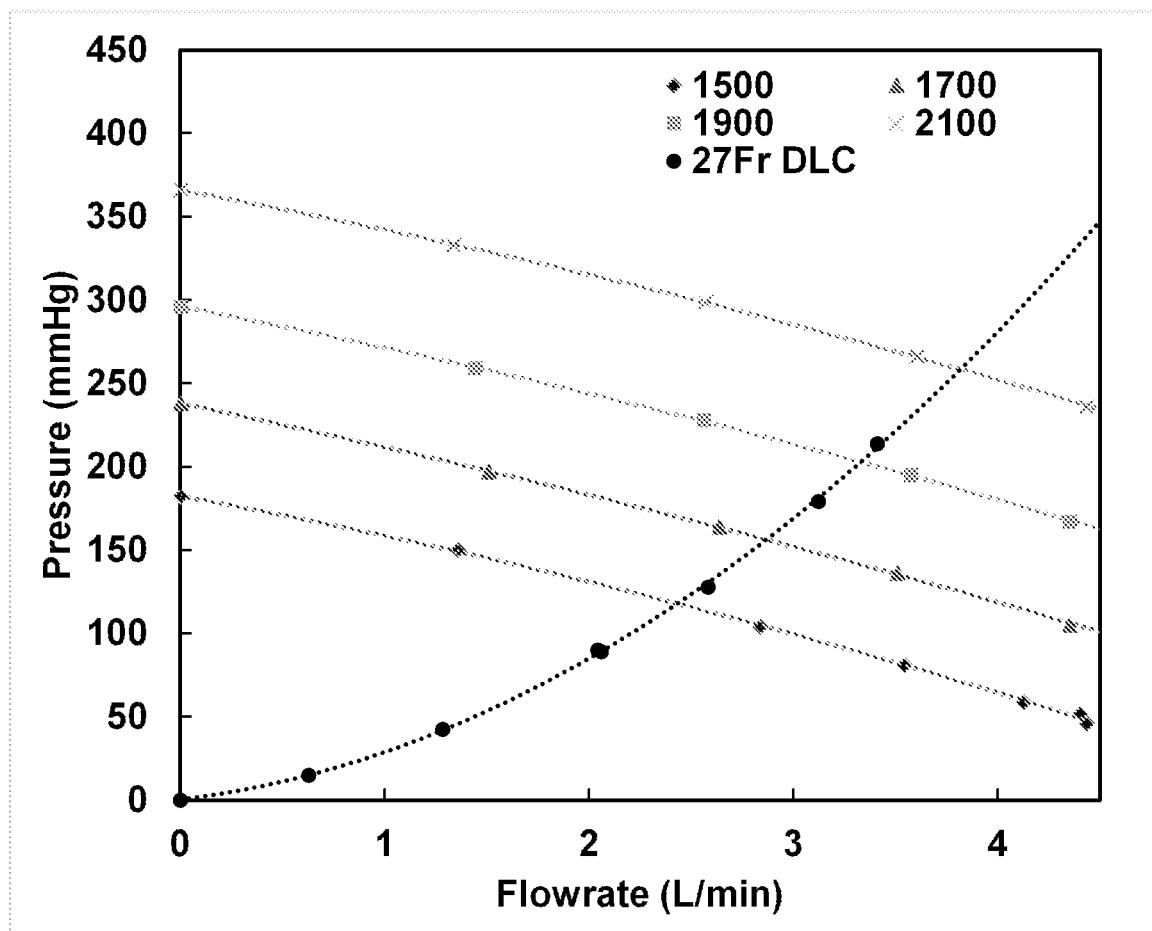
FIG. 15 illustrates a pump performance evaluation for the system of FIG. 11A.

FIG. 15 illustrates a pump performance evaluation for the paracorporeal ambulatory assist lung system 10a. The line through the data with filled black circles represents the required flow rate and pressure to be generated for the 27 French dual lumen cannula (DLC). The remaining lines set forth the generated flow rate and pressure of the system 10a at various impeller rotation rates in revolutions per minute. The intersection of the lines represent the operating points for the device. Sufficient pressure and flow is readily generated to pump against the cannula. Due to this pressure generation capacity, this device is capable of pumping more resistive cannula as well, which may exceed the resistance of the 27 French DLC by 50-100 mmHg at 3.5 L/min.

Figure 16:
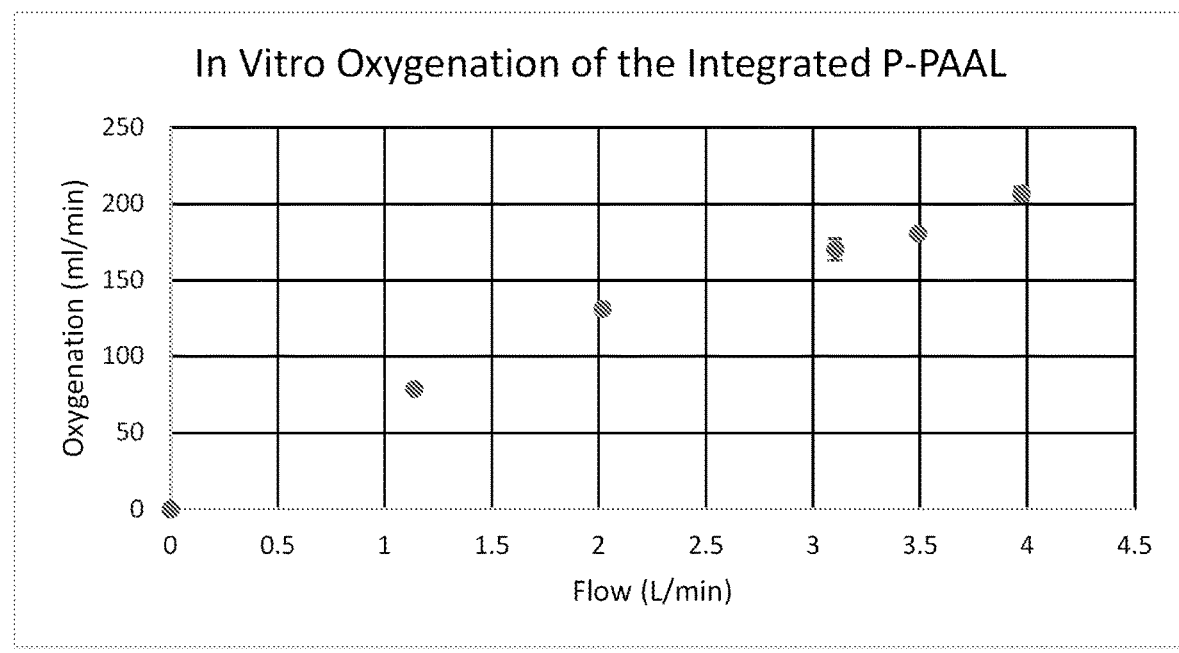
FIG. 16 illustrates a study of in vitro oxygenation of the paracorporeal ambulatory assist lung system of FIG. 11A wherein oxygenation is plotted as a function of flow rate.
Figure 17B:
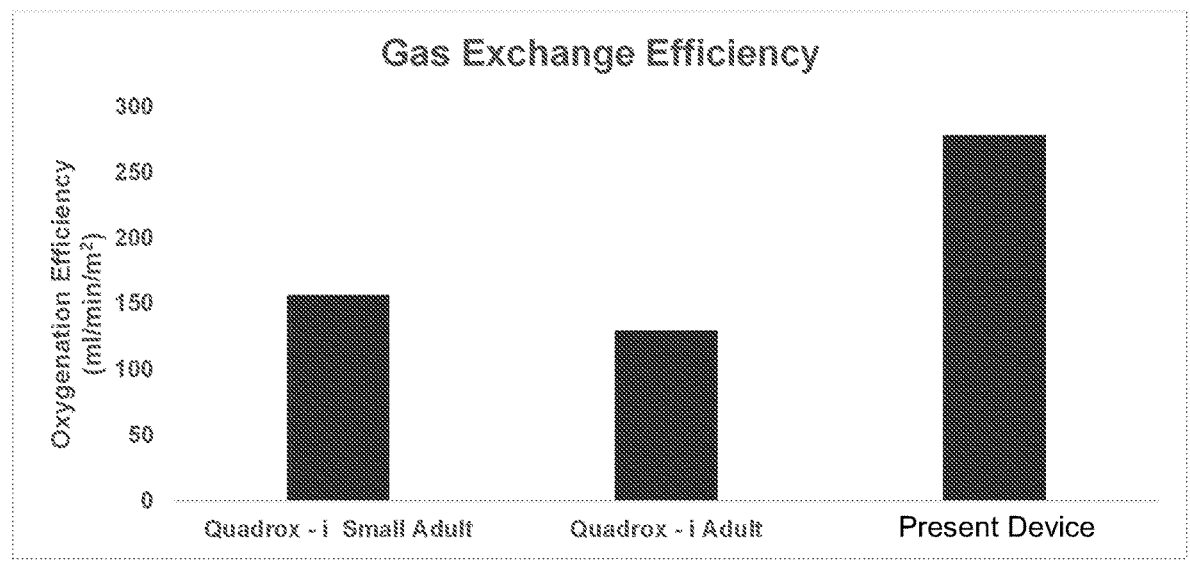
FIG. 17B illustrates a comparison of oxygenation efficiency (at a flow rate of 3.5 L/min) for the system of FIG. 11A and for two other systems.
Figure 17A:
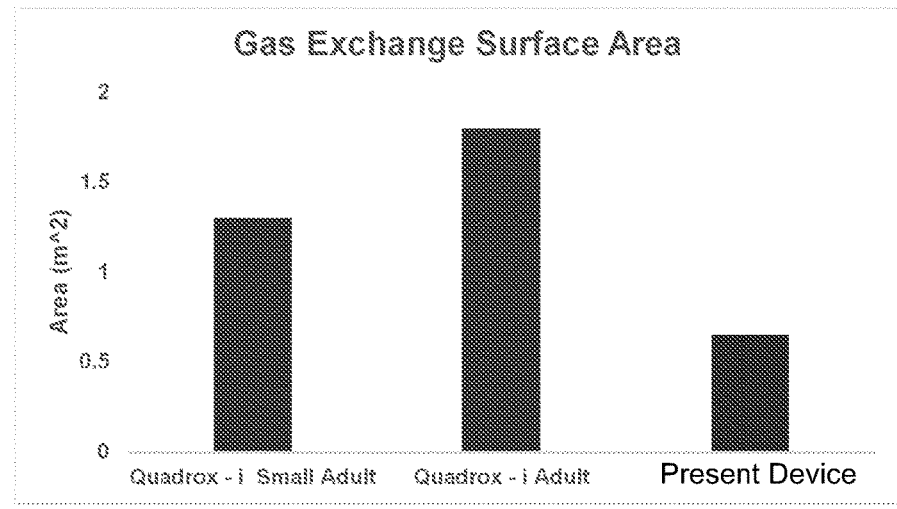
FIG. 17A illustrates a comparison of gas exchange surface area of the system of FIG. 11A and two other systems.

System 10 achieved a target oxygenation level of approximately 180 (ml/min) at flow rates in excess of approximately 3 L/min as illustrated in FIG. 16. FIG. 17A illustrates a comparison of gas exchange surface area of the system 10a and two other systems (the QUADROX-i® small adult and the QUADROX-i small adult oxygenators available from Maquet Cardiopulmonary GMBH Limited Liability Company of the Federal Republic of Germany). FIG. 17B illustrates that system 10 is significantly more efficient in oxygenation than either of the other two system of FIG. 17A. The flow rate was 3.5 L/min in the studies of FIG. 17B. The gas exchange surface area required in system 10a is thus significantly less than required in currently available devices.

Figure 18A:
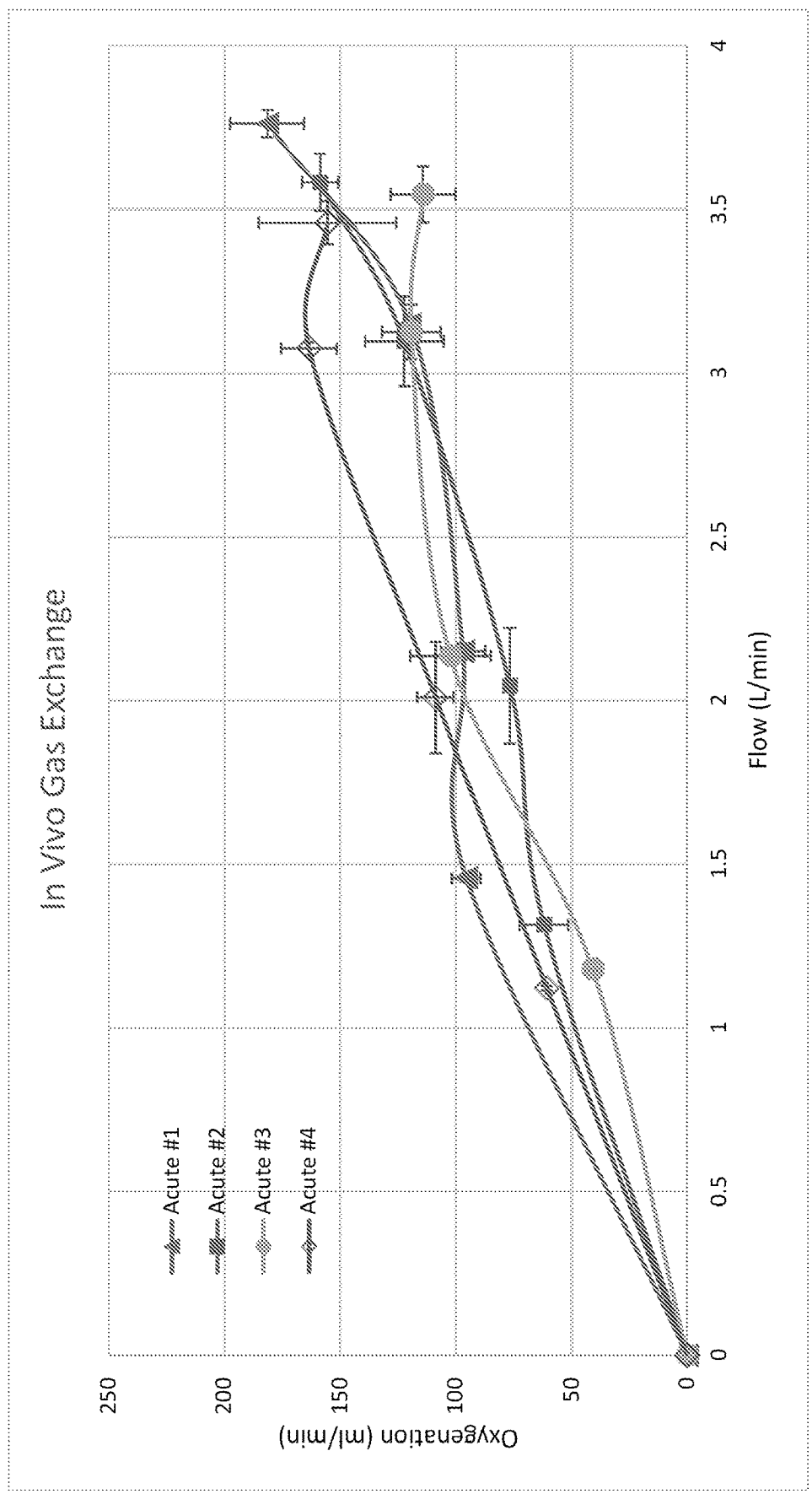
FIG. 18A illustrates a study of in vivo gas exchange/oxygenation of the system of FIG. 11A wherein oxygenation is plotted as a function of flow rate for four animal studies.
Figure 18B:
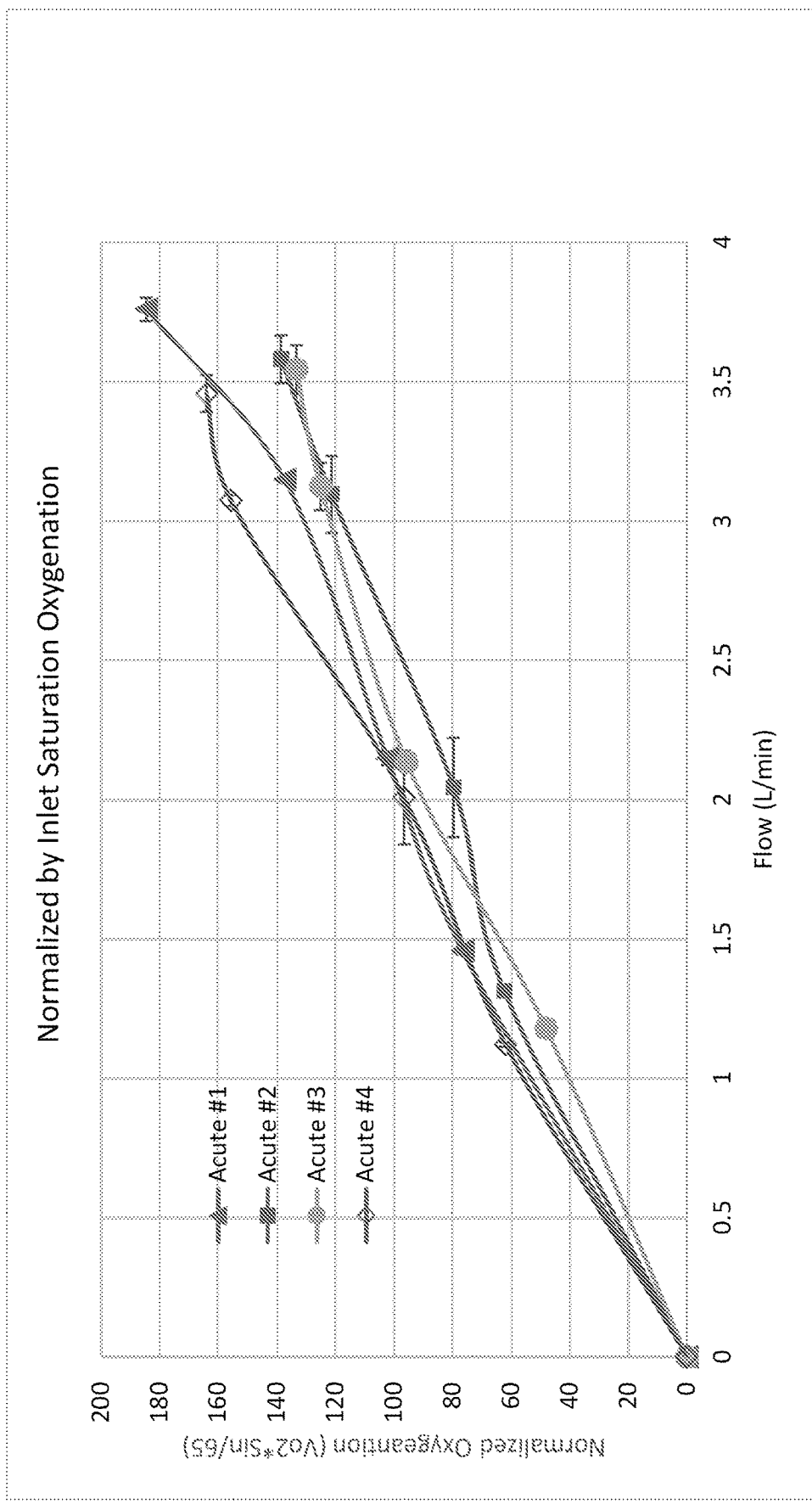
FIG. 18B illustrates a study of in vivo oxygenation normalized by inlet saturation oxygenation of the system of FIG. 11A wherein normalized oxygenation is plotted as a function of flow rate for four animal studies.

FIG. 18A illustrates a study of in vivo gas exchange/oxygenation of system 10A wherein oxygenation is plotted as a function of flow rate for four animal studies. FIG. 18A illustrates a study of in vivo oxygenation normalized by inlet saturation oxygenation of system 10a wherein normalized oxygenation is plotted as a function of flow rate for four animal studies. As flow rate increase, oxygenation increases with result similar to those obtained in bench studies. When blood left system 10a in each animal study, complete oxygenation was achieved (outlet saturation was 100%).

Figure 19:
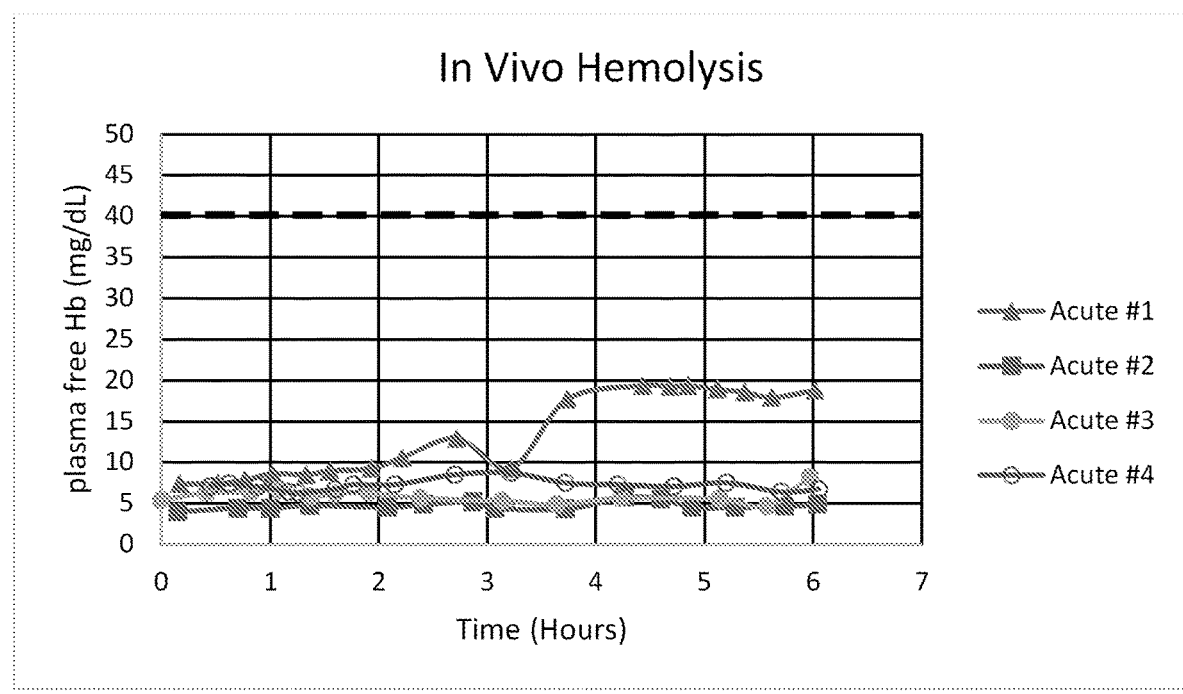
FIG. 19 illustrates of hemolysis in the system of FIG. 11A for four animal studies wherein plasma free Hb is plotted as a function of time.

FIG. 19 illustrates a study of hemolysis in system 10a for four animal studies wherein plasma free hemoglobin Hb is plotted as a function of time. The blood hemoglobin level was essentially flat in each animal study, indicating only moderate hemolysis which was well within acceptable levels. In the "acute" animal studies set forth in FIGS. 15 through 19, the studies lasted approximately 6 hours. No problems with thrombus occurred. Hemodynamic studies indicated that arterial pressure and central venous pressure during the studies were well controlled after 1 hour of the procedure.

In vitro pump tests were conducted in a solution of 8.5 g/L low viscosity carboxymethylcellulose (CMC) sodium salt (Sigma Aldrich, St. Louis, Mo.). A closed loop system using a 800 mL venous reservoir (Medtronic, Minneapolis, Minn.) kept at 37 C using a water bath connected to a PolyScience 210 heater (PolyScience Inc., Niles, Ill.). A hoffman's clamp was used to adjust afterload on the device while Honeywell 143 PC03D pressure transducers (Honeywell, Morris Plains, N.J.) were placed before and after the PAAL device to measure pressure drop while simultaneously determining flowrate using an ultrasound flow probe (Transonic Systems Inc., Ithaca, N.Y.). Studies were conducted at 1500, 1700, 1900 and 2100 RPMs to generate an H-Q curve. Pressure drop of the 27 Fr. Avalon ELITE® DLC (Maquet Cardiovascular LLC, Wayne, N.J.) was measured in a similar reservoir setup in which flow was driven with a Biomedicus BP 80-X pump (Medtronic, Minneapolis, Minn.) and pressure was measured at the inlet and outlet of the cannula.

Figure 20:
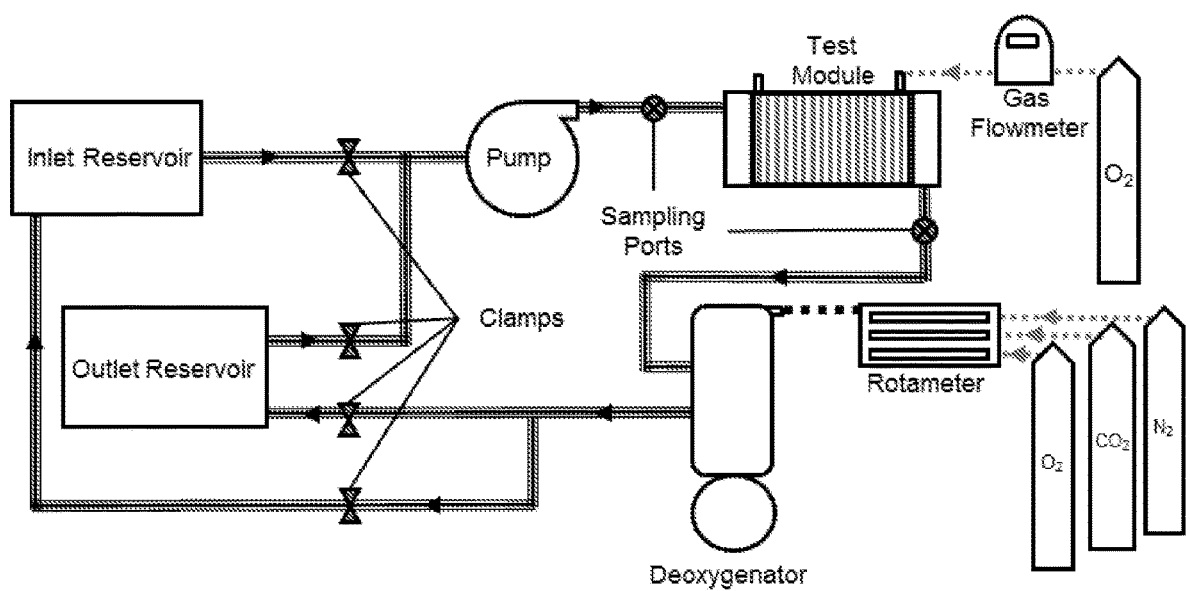
FIG. 20 illustrates an experimental setup for in vitro gas exchange studies.

In vitro gas exchange studies were performed in accordance with ISO 7199 standards. Seven liters of bovine or porcine blood is collected from a local slaughterhouse and heparinized (10 IU/mL). Blood is passed through a 40 μm filter (Pall Biomedical, Inc., Fajardo, PR) and gentamycin (0.1 mg/mL) is added to prevent bacterial growth. The experiment setup is a single pass loop system shown in FIG. 20. The loop consisted of two custom manufactured compliant six liter blood reservoir bags. The reservoirs were connected to a Biomedicus BP 80-X pump (Medtronic, Minneapolis, Minn.) which set loop flowrate. The test device is placed downstream of the pump, and a Medtronic Affinity NT 2.5 m² oxygenator (Medtronic, Minneapolis, Minn.) is downstream of the test device to remove oxygen added by the test device. The deoxygenator's built in heat exchanger is connected to a PolyScience 210 heater (PolyScience Inc., Niles, Ill.) maintaining blood temperature at 37 C. R-3603 Tygon tubing (Cole-Parmer, Vernon Hills, Ill.) connects circuit components. A blend of $N_2$, $CO_2$, $O_2$ sweep gas flowed through the deoxygenator conditioning blood, maintaining oxygen saturation of 65%±5 and $pCO_2$ of 45 mmHg±5. Once conditioned, blood passed from the inlet reservoir through the loop into the outlet reservoir such that the post device blood was separate from the conditioned blood at all times. One sample is drawn from each of the sampling ports shown in Figure C0-2. Samples are analyzed using a Rapid Point 405 Blood Gas Analyzer with Co-oximetry (Siemens Healthcare Diagnostics Inc., Tarrytown, N.Y.). An ultrasound flow probe (Transonic Systems Inc., Ithaca, N.Y.) measured blood flow. Pure oxygen sweep gas flows through the test device at 7.5 L/min, measured with a GR Series mass flow controller (Fathom Technologies, Georgetown, Tex.). Oxygen transfer rates are calculated using the following relationship:

$$\dot{V}_{O_2} = Q[\alpha_{O_2}(P_{O_2}^{out} - P_{O_2}^{in}) + C_T Hb \Delta S] \quad (3).$$

wherein $\dot{V}_{O_2}$ is the rate of oxygenation, Q is the blood flowrate, $\alpha_{O_2}$ the solubility of oxygen in blood $$\left(3 \times 10^5 \frac{ml_{O_2}}{ml_{blood} mmHg}\right), P_{O_2}^{out} - P_{O_2}^{in}$$

the partial pressure difference across the device, $C_T$ the binding capacity and $\Delta S$ the increase in oxygen saturation across the device.

In vivo acute studies were conducted in four 40-60 kg sheep for a duration of 6 hours. The animals were anesthetized using intramuscular Ketamine following which anesthesia was maintained with isoflurane inhalation. A swan-ganz catheter was placed in the pulmonary artery after which the animal was cannulated with the 27 Fr. DLC. After stabilization flowrate is varied between 1 and 4 L/min to determine gas exchange and flowrate relationships. Plasma free hemoglobin is measured every 30-60 minutes. Gross examination of the device and organs is done during necropsies.

As described above, magnets may be used for balancing the hydrodynamic load. If the hydrodynamic load exceeds the magnetic force beyond the threshold, the bearing system will fail. The orientation of the magnets in the system of PCT International Publication No. WO2014/085620 are part repelling and part attracting as a result of design constraints. Such a configuration does not allow one to reach high enough magnetic force to support high pressure pumping. In system 10 and 10a, however, all magnets may be oriented to be attracting allowing support of high pressure pumping. Relatively higher pressure pumping may, for example, allow use of an Avalon 27 Fr Dual Lumen cannula for flows exceeding 4 L/min. Increased pressure provided support a greater number of pathphysiologies.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. An extracorporeal system for lung assist comprising:
a housing, the housing comprising a blood flow inlet in fluid connection with a pressurizing stator compartment, a fiber bundle compartment in fluid connection with the pressurizing stator compartment via a flow channel formed within the housing in fluid connection with an inlet manifold of the fiber bundle compartment, and a blood flow outlet in fluid connection with an outlet manifold of the fiber bundle compartment;
an impeller rotatably positioned within the pressurizing stator compartment for pressurizing blood entering the pressurizing stator compartment from the blood flow inlet, the impeller centrifugally forcing blood radially outward into the flow channel which extends tangentially relative to the plane of rotation of the impeller from a volume of the pressurizing stator compartment around the impeller;
at least one generally cylindrical fiber bundle positioned within the fiber bundle compartment and comprising a plurality of hollow gas permeable fibers, the plurality of hollow gas permeable fibers being adapted to permit diffusion of gas between blood and an interior of the plurality of hollow gas permeable fibers, the plurality of hollow gas permeable fibers being positioned such that blood flows around the plurality of hollow gas permeable fibers when flowing through the at least one generally cylindrical fiber bundle compartment, the plurality of hollow gas permeable fibers extending generally perpendicular to the direction of bulk flow of blood which occurs generally axially through the fiber bundle compartment and generally axially through the at least one generally cylindrical fiber bundle positioned therein from the flow channel to the blood flow outlet,
a gas inlet in fluid connection with the housing and in fluid connection with inlets of the plurality of hollow gas permeable fibers, and
a gas outlet in fluid connection with the housing and in fluid connection with outlets of the plurality of hollow gas permeable fibers,
wherein an axis of the at least one generally cylindrical fiber bundle is oriented generally parallel to a plane of rotation of the impeller and the flow channel extends upward along a side of the housing from the pressurizing stator compartment to the inlet manifold so the blood is introduced into inlet manifold from the flow channel perpendicular to the axis of the at least one generally cylindrical fiber bundle and flow from the inlet manifold enters an end of the at least one generally cylindrical fiber bundle.

2. The system of claim 1 wherein the mean velocity of blood through the at least one generally cylindrical fiber bundle is at least 2 cm/sec.

3. The system of claim 2 wherein a cross-sectional area of the at least one generally cylindrical fiber bundle is no more than 3.14 in$^2$.

4. The system of claim 2 wherein a cross-sectional area of the at least one generally cylindrical fiber bundle is no more than 2.4 in$^2$.

5. The system of claim 2 wherein a length of the at least one generally cylindrical fiber bundle is at least 1.8 inches.

6. The system of claim 1 wherein the at least one generally cylindrical bundle is formed from a plurality of layers of fiber fabric, each of the plurality of layers of fiber fabric comprising hollow gas permeable fibers.

7. The system of claim 6 wherein blood is blocked from flowing to the gas inlet and the gas outlet.

8. The system of claim 6 wherein adjacent layers of fiber fabric are rotated relative to each other such that the orientation of the plurality of hollow gas permeable fibers in adjacent layers of fiber fabric are of a different orientation.

9. The system of claim 1 wherein the system is adapted to deliver flows in the range of approximately 2 to 4 liters per minute.

10. The system of claim 9 wherein the flow is adjustable.

11. The system of claim 1 wherein the flow channel is dimensioned to conserve cross-sectional area between the blood flow inlet and the flow channel.

12. The system of claim 11 wherein the flow channel extends in a curved path from the pressurizing stator compartment to the inlet manifold.

13. The system of claim 1 wherein the flow channel extends in a curved path from the pressurizing stator compartment to the inlet manifold.

14. The system of claim 13 wherein a cross-sectional area of the at least one generally cylindrical fiber bundle is no more than 7.07 in$^2$.

15. The system of claim 1 wherein the system is a paracorporeal system.

16. The system of claim 1 wherein the housing is no more that 12.7 cm in height, no more than 12.7 cm in width, and no more than 12.7 cm in length.

17. The system of claim 1 wherein the mean velocity of blood through the at least one generally cylindrical fiber bundle is at least 3 cm/sec.

18. The system of claim 1 wherein the mean velocity of blood through the at least one generally cylindrical fiber bundle is in the range of approximately 2 to 5 cm/sec.

19. The system of claim 1 wherein the blood flow inlet is in connection with the pressurizing stator compartment via a plenum.

20. The system of claim 1 wherein the flow channel has a stadium cross section or a circular cross section over a portion thereof extending upward along a side of the housing.

21. A method of extracorporeal lung assist to a patient, comprising:
providing a system comprising a housing, the housing comprising a blood flow inlet in fluid connection with a pressurizing stator compartment, a fiber bundle compartment in fluid connection with the pressurizing stator compartment via a flow channel formed within the housing in fluid connection with an inlet manifold of the fiber bundle compartment, and a blood flow outlet in fluid connection with an outlet manifold of the fiber bundle compartment, an impeller rotatably positioned within the pressurizing stator compartment for pressurizing blood entering the pressurizing stator compartment from the blood flow inlet, the impeller centrifugally forcing blood radially outward into the flow channel which extends tangentially from a volume of the pressurizing stator compartment around the impeller, at least one generally cylindrical fiber bundle positioned within the fiber bundle compartment and comprising a plurality of hollow gas permeable fibers, the plurality of hollow gas permeable fibers being adapted to permit diffusion of gas between blood and an interior of the plurality of hollow gas permeable fibers, the plurality of hollow gas permeable fibers being positioned such that blood flows around the plurality of hollow gas permeable fibers when flowing through the fiber bundle compartment, the plurality of hollow gas permeable fibers extending generally perpendicular to the direction of bulk flow of blood generally axially through the fiber bundle compartment and generally axially through the at least one generally cylindrical fiber bundle positioned therein from the flow channel to the blood flow outlet, a gas inlet in fluid connection with the housing and in fluid connection with inlets of the plurality of hollow gas permeable fibers, and a gas outlet in fluid connection with the housing and in fluid connection with outlets of the plurality of hollow gas permeable fibers, wherein an axis of the at least one generally cylindrical fiber bundle is oriented generally parallel to a plane of rotation of the impeller and the flow channel extends upward along a side of the housing from the pressurizing stator compartment to the inlet manifold so the blood is introduced into inlet manifold from the flow channel perpendicular to the axis of the at least one generally cylindrical fiber bundle and flow from the inlet manifold enters an end of the at least one generally cylindrical fiber bundle;
connecting the blood flow inlet to the patient's vasculature;
connecting the blood flow outlet to the patient's vasculature; and
passing a sweep gas within lumens of the plurality of hollow gas permeable fibers via the gas inlet and the gas outlet.

22. The method of claim 21 wherein the system is operated as a paracorporeal system.

* * * * *

UNITED STATES PATENT AND TRADEMARK OFFICE
CERTIFICATE OF CORRECTION

PATENT NO. : 11,045,597 B2
APPLICATION NO. : 15/738406
DATED : June 29, 2021
INVENTOR(S) : Shalv Madhani et al.

It is certified that error appears in the above-identified patent and that said Letters Patent is hereby corrected as shown below:

In the Specification

Column 1, Line 17, delete "DK078775".

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*